United States Patent [19]
Hall

[11] Patent Number: 5,195,985
[45] Date of Patent: Mar. 23, 1993

[54] SYRINGE HAVING A RETRACTABLE NEEDLE

[76] Inventor: John E. Hall, 5751 Richards Cir., Shawnee, Kans. 66216

[21] Appl. No.: 528,592

[22] Filed: May 25, 1990

[51] Int. Cl.⁵ .............................................. A61M 5/32
[52] U.S. Cl. .................................. 604/195; 604/110; 604/232; 604/264; 604/263
[58] Field of Search ............... 604/110, 188, 195, 221, 604/232, 239, 240, 192, 198, 241, 263, 264

[56] References Cited

U.S. PATENT DOCUMENTS

| | | | |
|---|---|---|---|
| 4,747,830 | 5/1988 | Gloyer et al. | 604/110 |
| 4,804,370 | 2/1989 | Haber et al. | 604/195 |
| 4,909,794 | 3/1990 | Haber et al. | 604/195 |
| 4,919,652 | 4/1990 | Alter et al. | 604/110 |
| 4,931,040 | 6/1990 | Haber et al. | 604/110 |
| 4,932,939 | 6/1990 | Magre et al. | 604/110 |
| 4,978,340 | 12/1990 | Terrill et al. | 604/195 |
| 4,986,813 | 1/1991 | Blake et al. | 604/110 |
| 4,995,874 | 2/1991 | Strickland | 604/195 |
| 5,030,208 | 7/1991 | Novacek et al. | 604/195 |

*Primary Examiner*—C. Fred Rosenbaum
*Assistant Examiner*—Corrine Maglione

[57] ABSTRACT

This invention is directed to improved syringes and protected needle accessories for use in injecting or withdrawing fluids as well as catheter placement use. Needles are encapsulated for proper disposal after use is complete. Accessories include syringes, catheters, filters, guide wires, dental cartridge-needle combinations and medication-laden syringes, blood drawing needles, holders and biopsy needles. Devices help combat drug abuse and disease transmission by safely isolating the needle point. Containment shells, caps, case accessories, and self-annulling plugs are provided to protect the user and innocent bystander from needle and contaminating fluids. Superior sealing means are disclosed and a tactile securing means to fasten a needle or cap to a threaded hub or collar. Standard parts are used where possible. Self-aspirating capability is provided in some cases. In some medication-laden syringe containment systems, a coaxial cap-needle is first segregated from and later fastened to the eye opening of the eye cap cover of the containment means. A cap-handle device may be used to safely recap an exposed and unprotected needle.

12 Claims, 10 Drawing Sheets

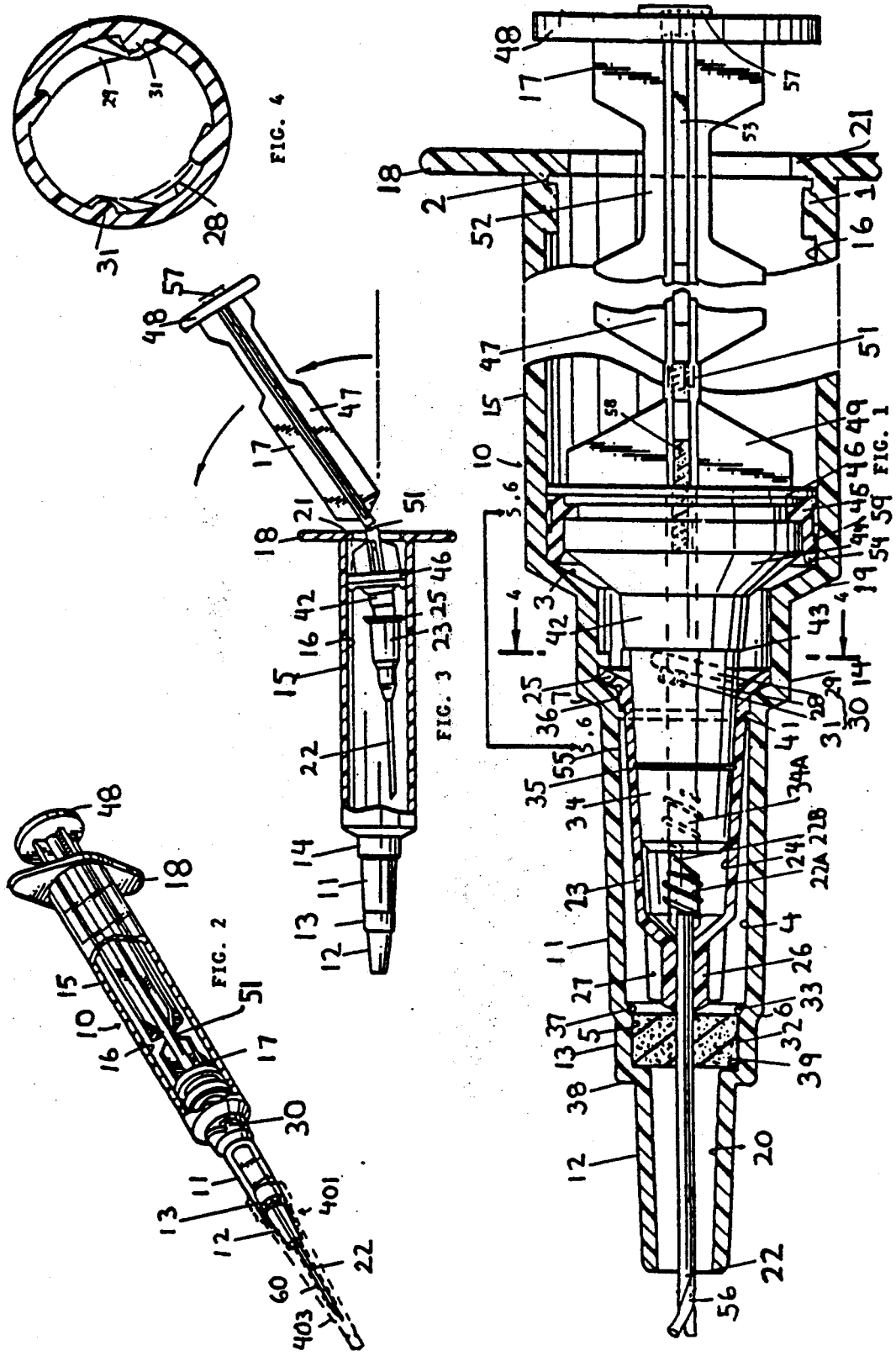

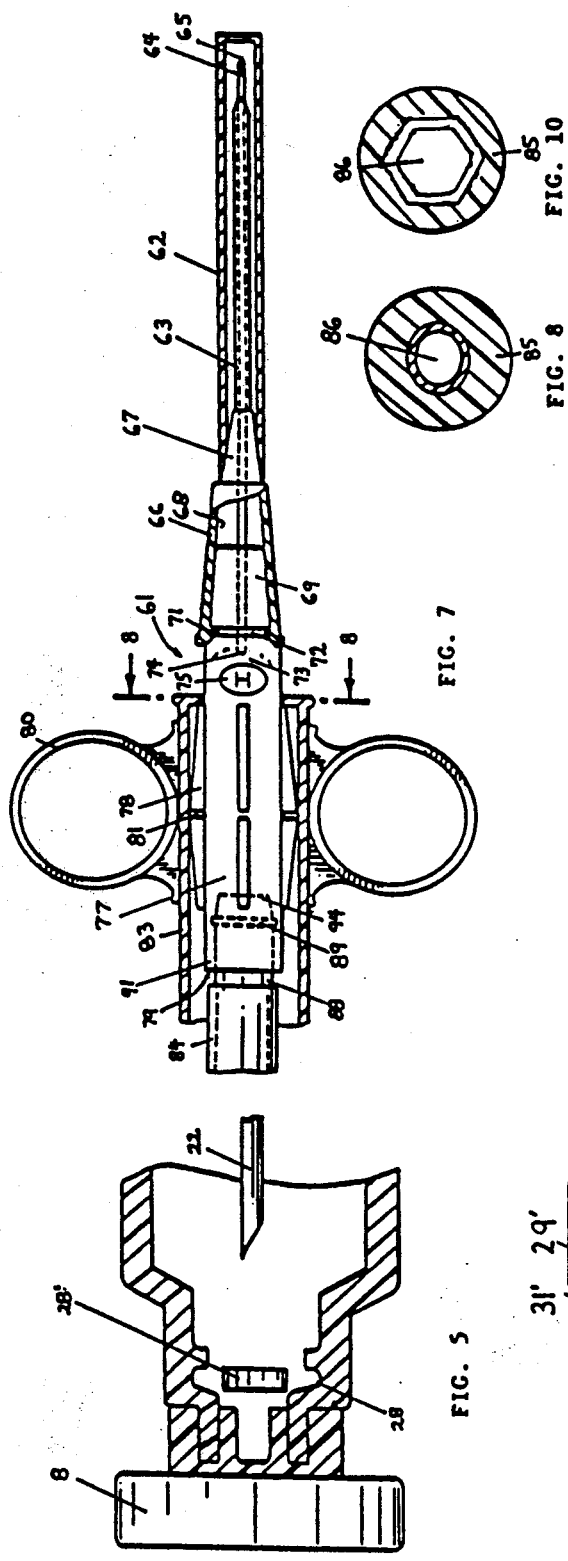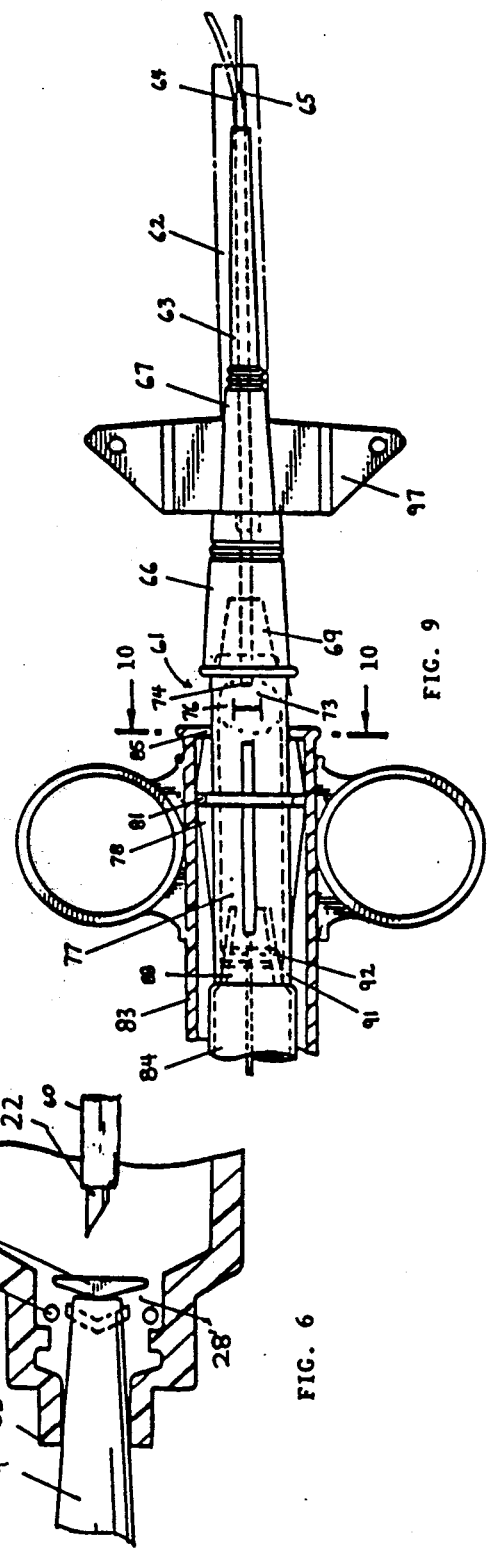

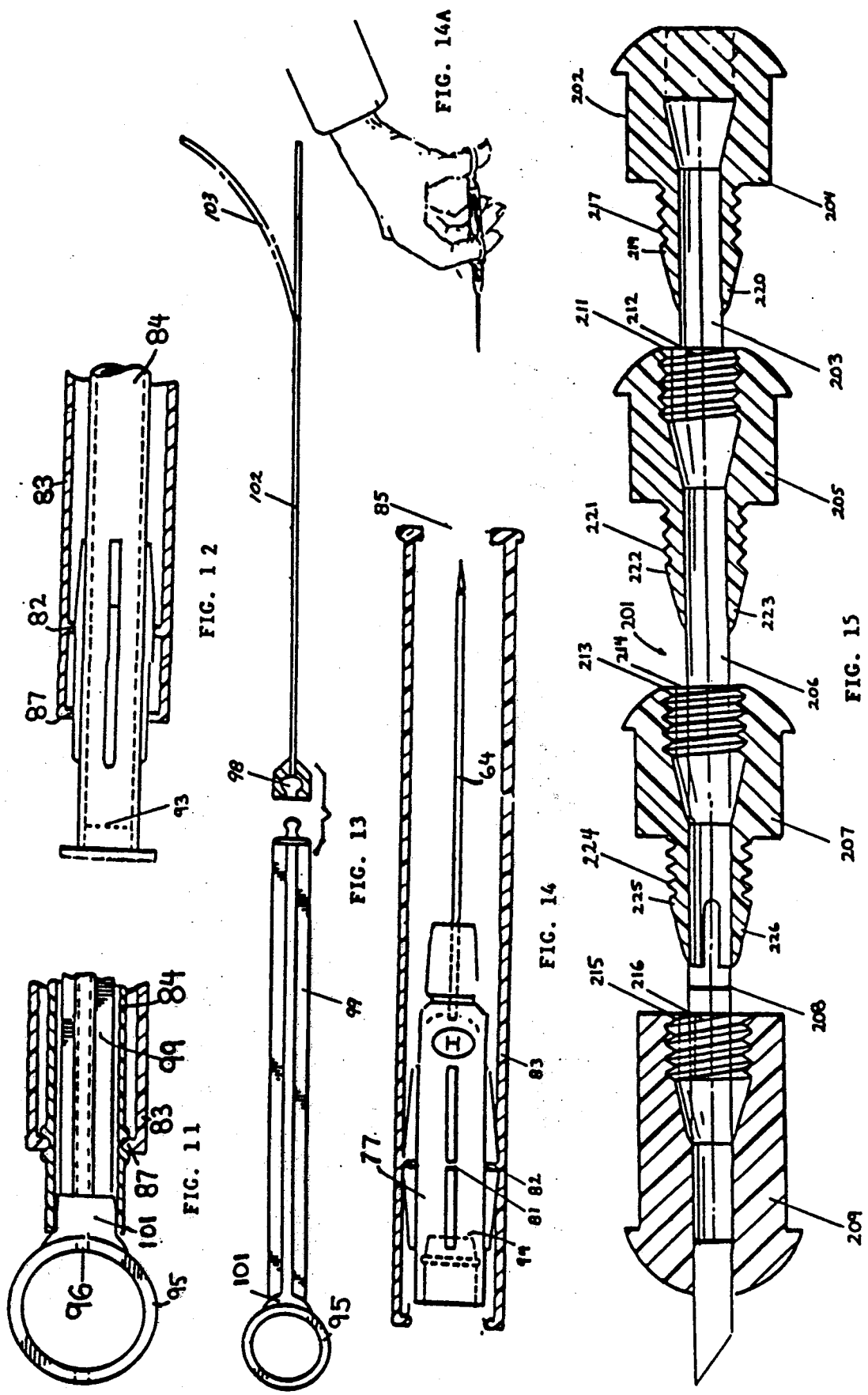

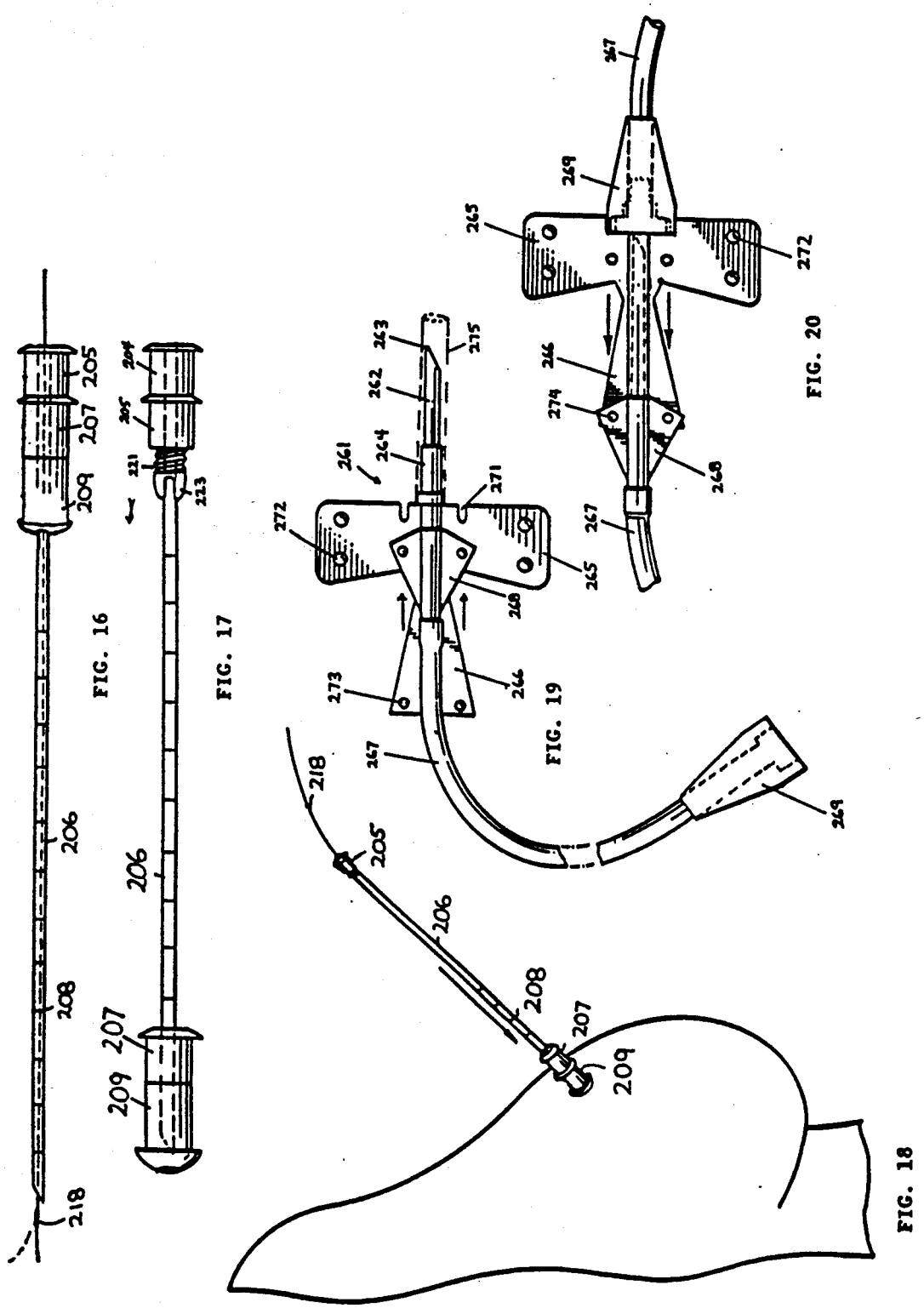

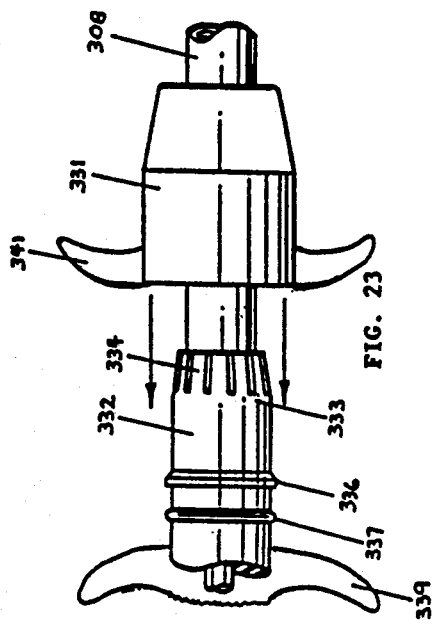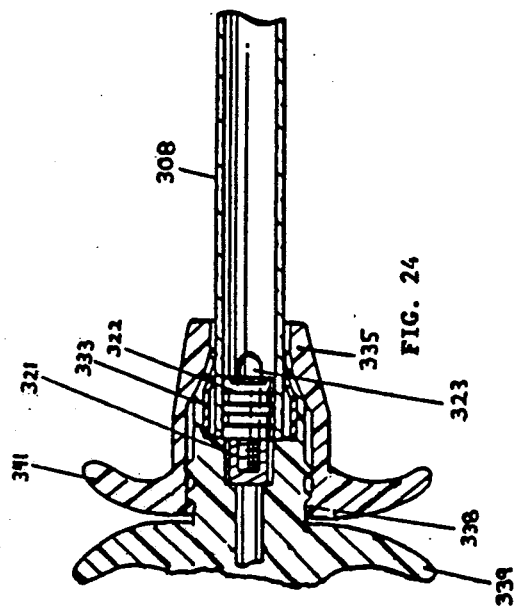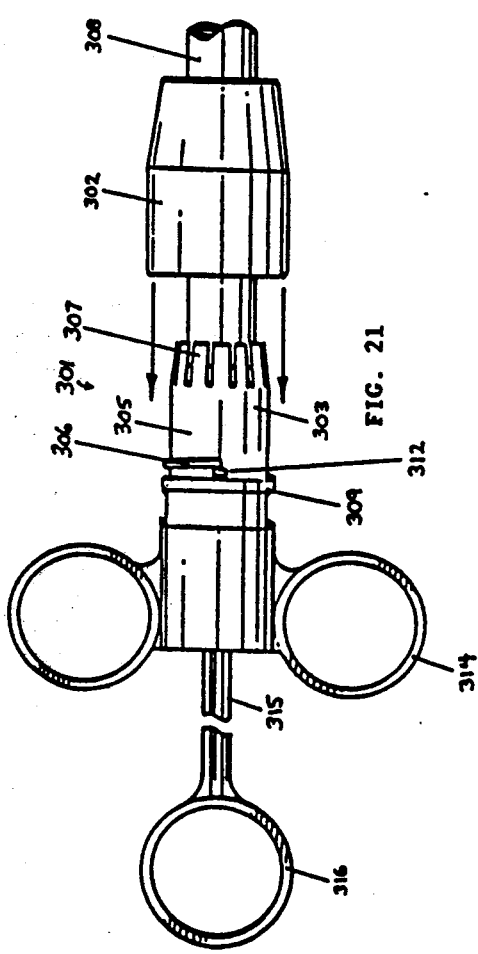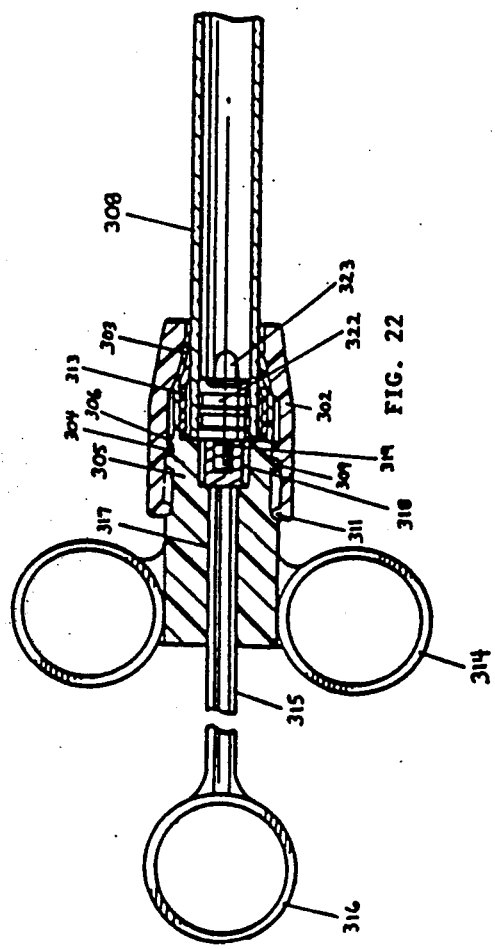

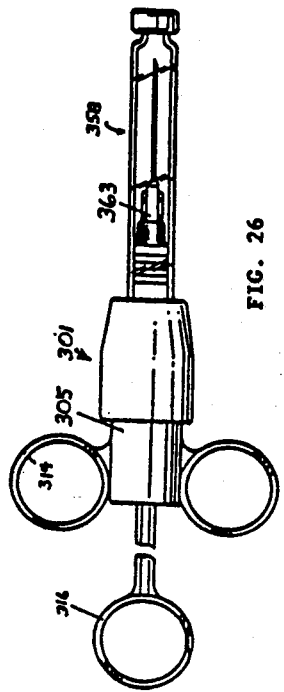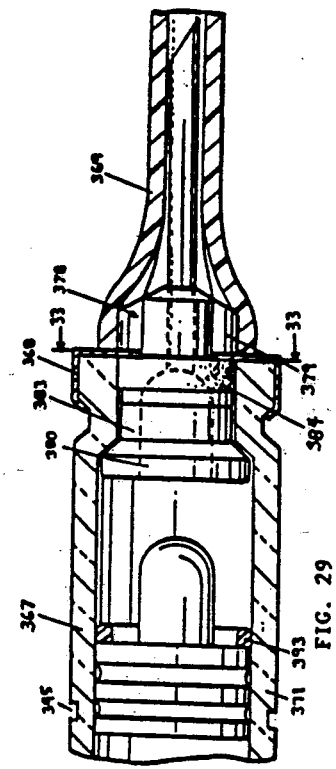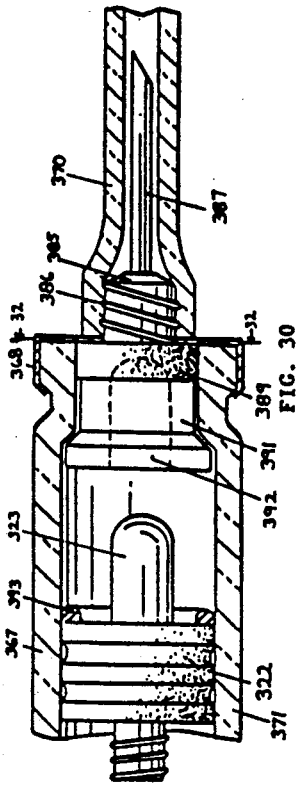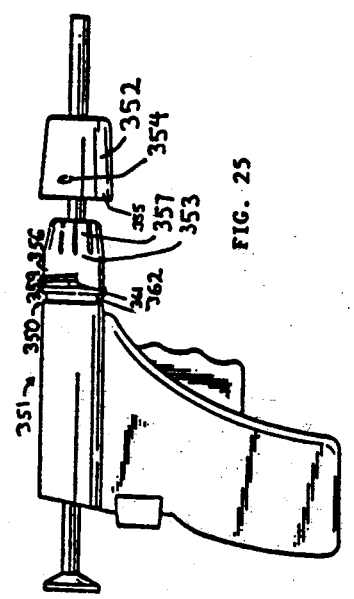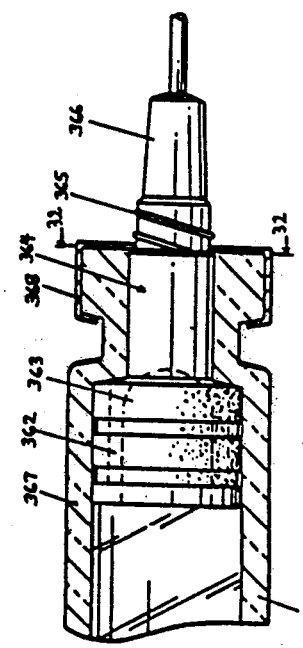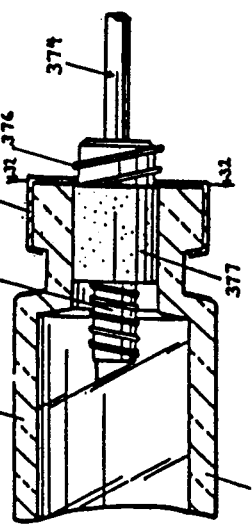

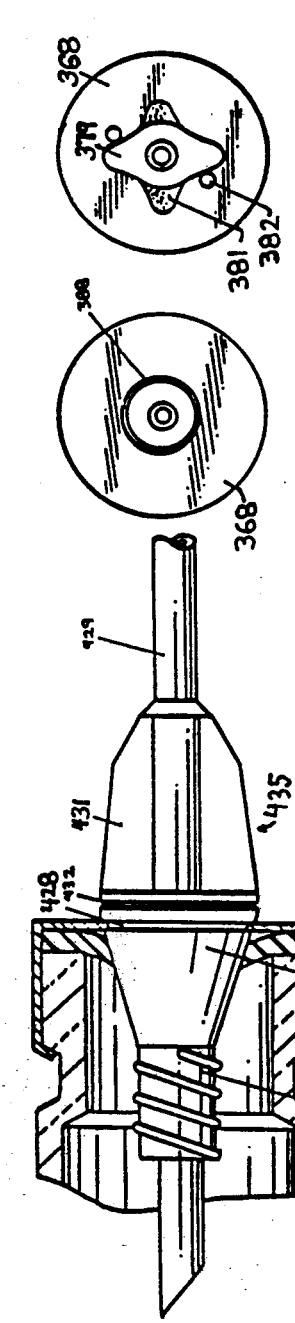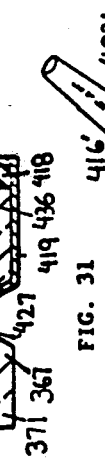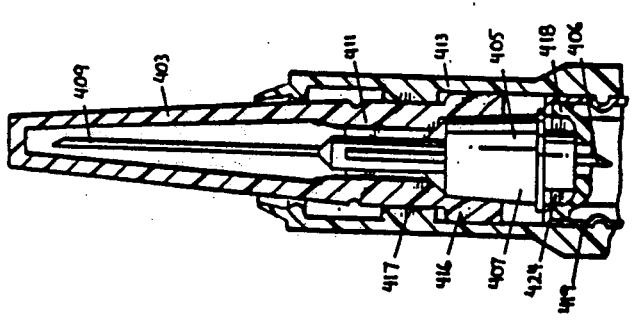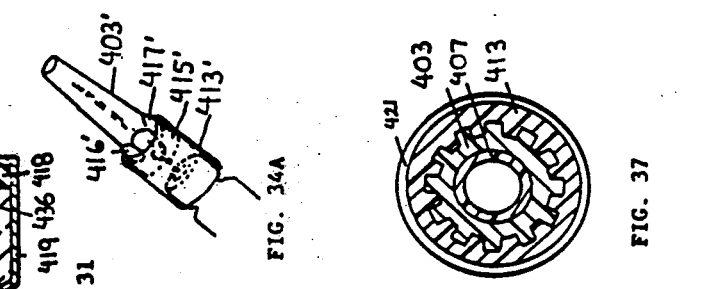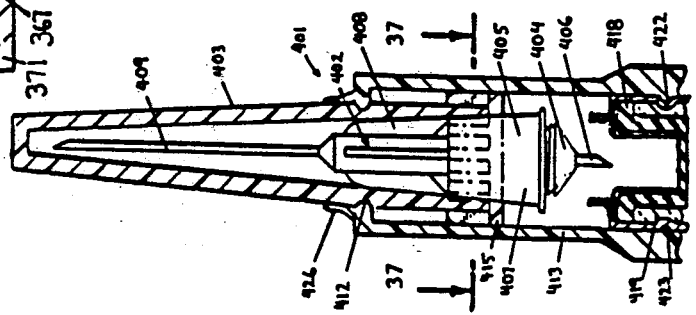

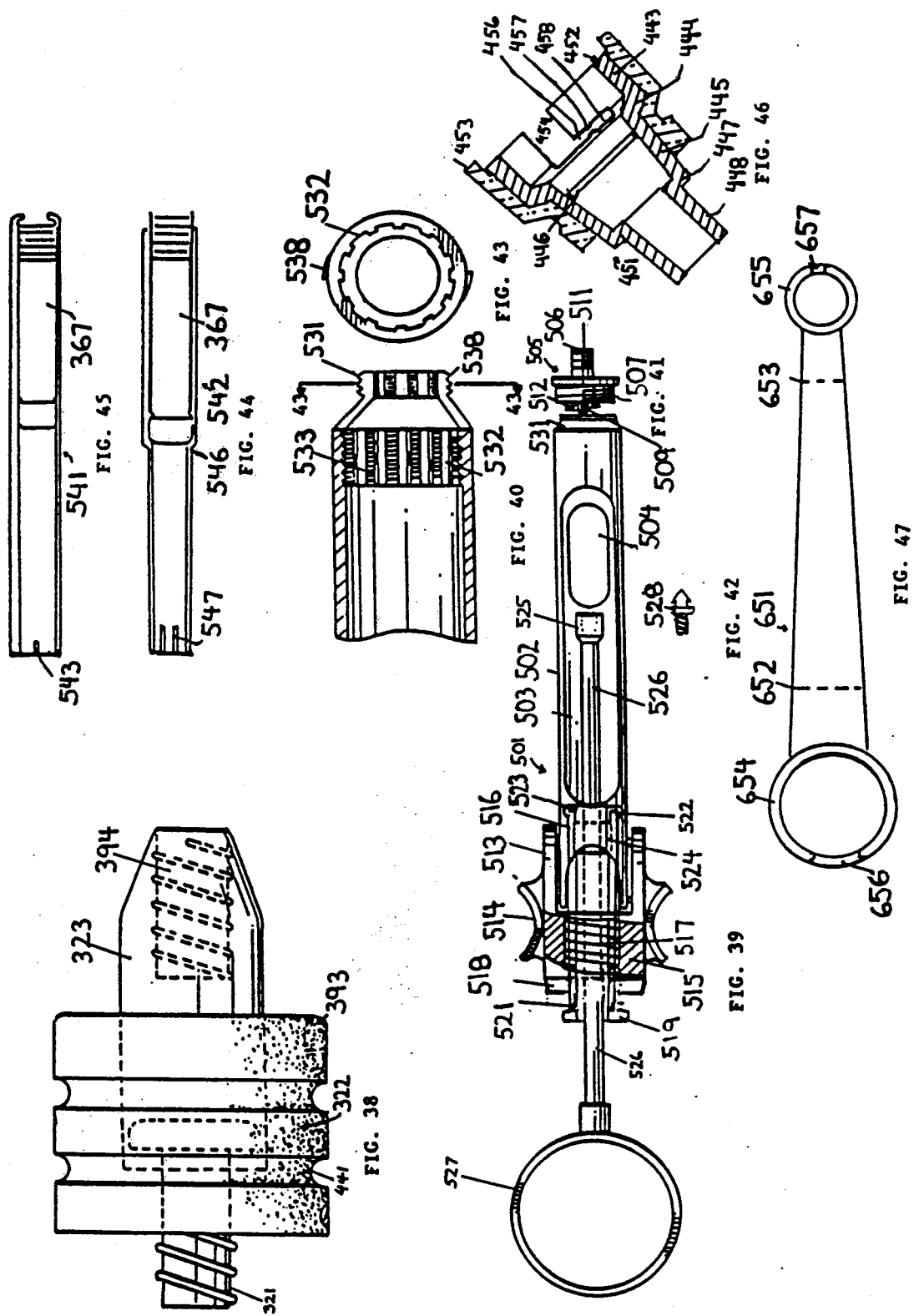

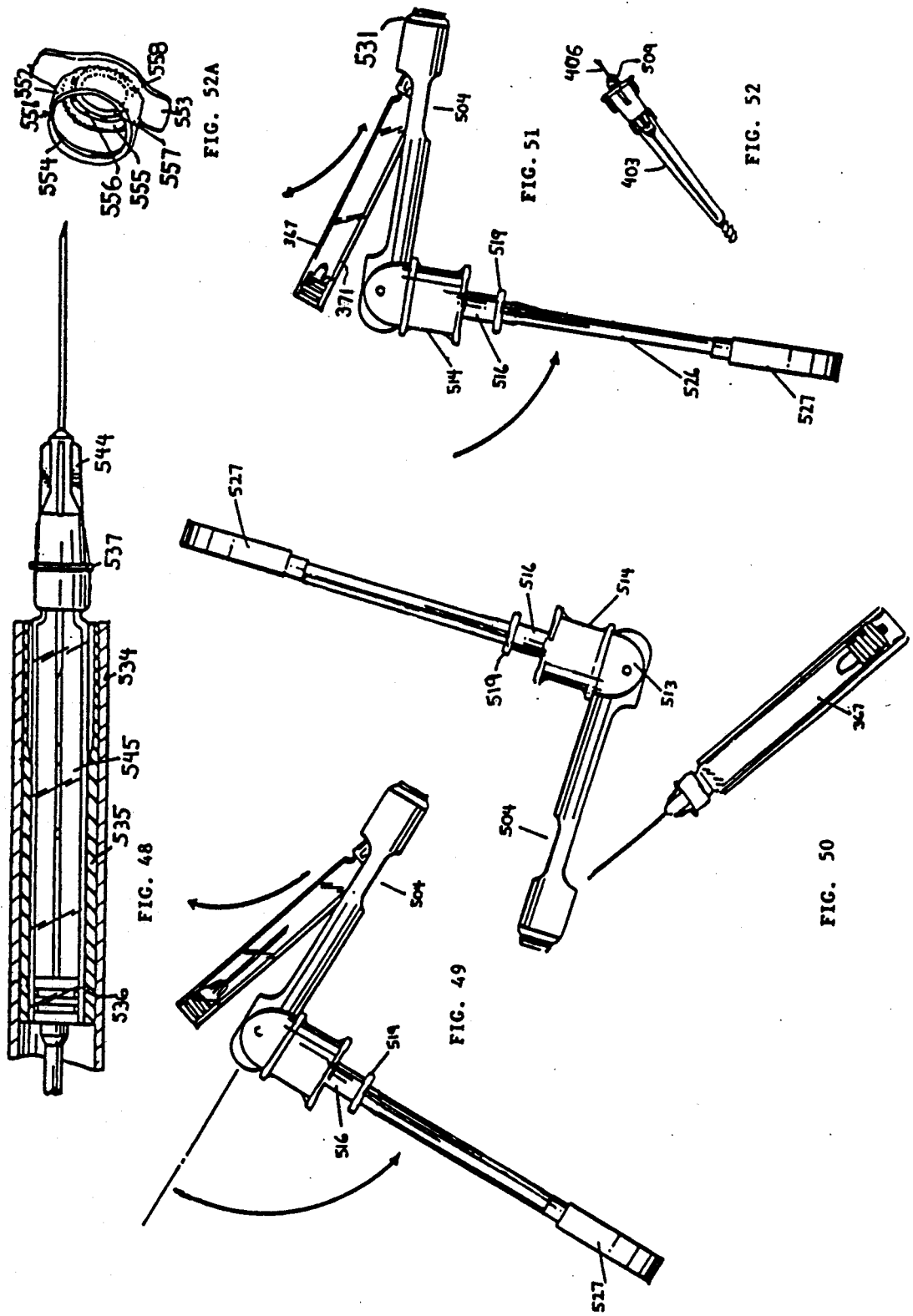

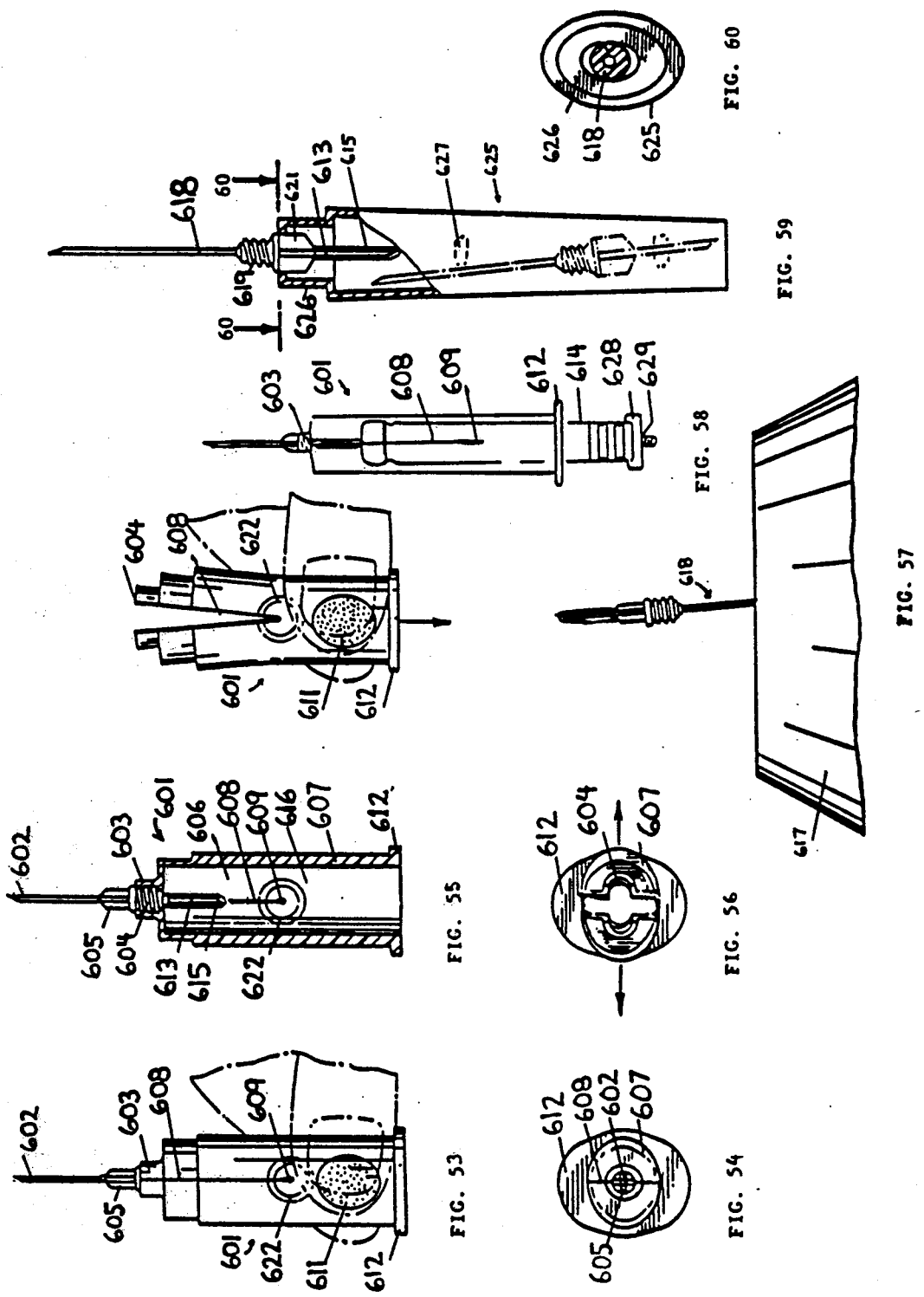

SYRINGE HAVING A RETRACTABLE NEEDLE

BACKGROUND OF THE INVENTION

This invention relates to disposable syringes and needle containing appliances for use in injecting or withdrawing fluids. They are adapted to prevent accidental needle-stick injury by encapsulation of needles for proper disposal after use is complete. The term syringe denotes an instrument used for injecting or aspirating fluids.

In the health care field, health care workers such as nurses and other professionals, as well as related personnel such as house keeping staff and the like, are subject to "stick-needle" injury. A needle-stick occurs whenever a needle passes through the skin of a person by intension or by accident. Disposable medical devices are often used which contain needles for subcutaneous injection, for gaining access to a person's blood vasculature for therapeutic administration of a blood product or medication delivery, or for obtaining a sampling of blood from a patient for analysis. Current devices being utilized provide incentives for health care workers to either recap or clip or otherwise protect needles after use of the device is complete. It is often after use is complete and prior to disposal that workers are most at risk from accidental and self-inflicted needle-stick injury. Even if needles are carefully discarded without being protected and the primary health care provided escapes injury, the cleaning staff or other innocent bystanders are very often still at risk. Before needles can be incinerated or properly buried in a landfill, human contact is possible and occurs frequently. Needles are contaminated once used with nosocomial germs such as the hepatitis or AIDS virus. Each and every used needle poses a potential threat of transferring dangerous microorganisms both inside the hospital and in the community. Availability of operable used disposable needle containing devices is a contributing cause of repeat drug abuse where syringes are shared and also a key factor in disease transmission. A needle-stick injury, when reported, is usually followed by a shot of passive immunizing agent to reduce the chance of contracting hepatitis or tetanus infection. There is no known immunoglobulin or anti-serum for the treatment of the HIV AIDS ARC retroviruses. Therefore, prevention of needle-stick injury has become of paramount importance. Blood donors or potential AIDS patients are entitled to their privacy and even if tested, may test negatively for AIDS or other diseases during the incipient stages. Such persons receiving a needle-stick may engage in subsequent behavior which would unknowingly transmit the virus—even in doing something as harmless and seemingly altruistic as making a blood donation. Precautionary measures when taken, result in discomfort and apprehension by the recipient as well as added cost to the responsible health care facility. Unfortunately, needle-stick injury is a "no win" situation and will likely take on added importance as times passes. Knives and swords are housed in protective scabbards when not in use. Just as guns are required to be holstered and permits obtained in their responsible use, a needle may begin to take on the same or similar lethal significance. This strengthens the argument for cost effective sealed encapsulation after use is complete..

Numerous modified disposable needle containing appliances such as syringes, catheters and dental or medical hypodermic syringes have been discovered in recent years to lessen the likelihood of needle-stick injury. Alternative disposable needle holders, syringes or other appliances may be rendered inoperable after use to combat drug abuse and disease transmission.

Janine Jagger, MpH, PhD, an assistant professor of Neuro-surgery from the University of Virginia Medical Center, gave testimony in Washington D. C. before the Department of Labor, Occupational Safety and Health Administration (OSHA) board to consider guidelines and rules on occupational exposure to bloodborne pathogens on Sep. 12. 1989. Dr. Jagger authored a study published in the New England Journal of Medicine, August 1988 issue, and disclosed a table listing six major devices causing needle-stick injuries as well as way in which the injuries occurred. Dr. Jagger has learned how to make projections of potential reductions in needle-stick injury following specific design modifications. Devices listed included:

(1) Disposable syringes, being responsible for ⅓ of all needle-stick injuries and ¼ of those injuries from attempts to recap used needles.

(2) Prefilled cartridge syringes where injury was related to disassembly or improper disposal of needles.

(3) Winged intravenous catheters with tubing for fluid infusion or blood sampling where workers receive a stick when disposing of the winged needles and tubing.

(4) The catheter placement unit used to gain access to the vascular system wherein the catheter is inserted into a vessel and the rigid stylet or needle removed and disposed of quickly so that the unprotected needle poses a hazard to housekeeping staff as well as other workers and patients.

(5) The vacuum tube holder which is most often used for drawing blood, and the phlebotomy needle must be wrenched from the reusable holder after use. Health care workers often recap these needles to save time in disposal and to guard against needle-stick injury prior to disposal.

Inadvertent detachment of intravenous lines and subsequent dangling tubing with needles attached have been a problem in past years. Surgical tape has been a make shift solution to secure the connections. This denotes poor product design as well as inattention to the needle-stick hazard and has resulted in may needle-stick injuries. Methods to shroud or otherwise sheath the needles to protect them have been obvious solutions. In some cases, needles have been eliminated altogether from such tubing and systems. Dr. Jagger found that rates of needle-stick injury were highest for devices requiring disassembly after use. These are the last five devices as mentioned above and injury can be attributed to a lack of protection for the worker's hands during disassembly.

Product structure improvements will solve the needle-stick injury problem. Optimal solutions will eliminate needles from designs where possible or minimize their use. Otherwise, needles should always remain covered by a shroud or encapsulation means or ferrule or barrel with an open end for receiving whatever needs to have contact with the point of a needle ie. injection cap or medication vial membrane. Membranes must be penetrated in non-coring fashion. Unless the industry gravitates to standard packaging, such approaches would not always be practical. Because of the large variety of uses and requirements for needles, other means must be found to protect exposed needles. Jagger believes that best designs should be incorporated into a device instead of being provided as a separate accessory. A device should provide protection prior to disassembly and should remain in effect after disposal to protect the waste handler, as well as others who may encounter the device. Such safety designs should be simple to use and require little training to use effectively. Any incentive to make further use of a used device should be removed. A disposable device should be irreversible. Any change should not increase manufacturing cost of difficulty in use. Device disposal should automatically comply with OSHA recommendations. These include that needles should not be recapped, purposely bent or broken by hand, removed from disposable syringes or otherwise manipulated by hand. After they are used, disposable syringes and needle should be placed in puncture resistant containers. Such containers shall be constructed so that they will not spill their contents if knocked over and will not themselves allow injuries when handled. It is important that such containers by located on patient floors or any other setting where blood is drawn and needles are handled. Prior art devices that appear to be inconsistent with recommendations include U.S. Pat. Nos. 4,695,274 to Fox; 4,610,667 to Pedicano; 4,596,562 to Venon; and 4,573,976 and 4,425,120 to Sampson.

In particular, devices that protect a needle after use is complete may be divided into two categories. First, there are devices that assist the user in resheathing or recapping the needle after use. These provide for replacing a detachable cap or sheath without the user's hands coming into proximity to the needle point or otherwise contain a movable ferrule or cylinder which may be moved axially along the syringe and relocated around the needle to cover and protect the point. The second category of devices developed to protect needles incorporates various mechanisms for retracting the needle into the syringe barrel or into a protective case. U.S. Pat. Nos. 4,676,783 and 4,781,692 to Janine C. Jagger illustrate winged retractable safety needles. It is pointed out that winged safety needles are currently recapped using the same cover that is provided in the packaged product. Such products encourage hand movement toward needle points and thus, needle-stick injury. Jagger points to protection for winged needles or catheters by providing a rigid housing proximal to the wings into which the needle may be withdrawn after use is complete. This occurs when the user pulls on the hub end and tubing or tabs thereof to retract the needle into the protective housing. It is not clear how well the needle is anchored in both the exposed and retracted position. Although the needle may be protected in this manner, it is possible that such needles may become inadvertently exposed during or after disposal because a lock of the retracted needle is not provided. If applied to catheter placement unit use, such a concept should also provide a viewing means of blood flashback. Such a device must be irreversible. The instant invention provides for such shortcomings in a cost effective manner.

Devices that assist the user in recapping or resheathing the needle do not go far enough to render the device inoperable. Recap devices that cannot make use of standard parts may be lost and slide sheaths often inadvertently retract to leave the unprotected needles of such devices exposed. Besides the extra expense for additional parts an time lost in cumbersome manipulation, such devices are inconvenient and expensive. Devices in this category include U.S. Pat. Nos. 4,610,667 to Pedicano; 4,596,562 to Vennon; and 4,573,976 and 4,425,120 to Sampson and 4,795,443 to Peach.

Prior retractable needle devices have shortcomings. Some devices require partial assembly such as U.S. Pat. Nos. 4,710,170 to Haber and 4,592,744 to Jagger. This is potentially confusing, and disassembled parts may become contaminated and unprotected. A primary shortcoming of most retractable needle syringes is that each requires use of non-standard needle support structures ie. a needle and base that must be specifically manufactured as opposed to using standard parts known to the medical industry. This results in a lack of interchangeability with available needle configurations and added cost, besides lack of familiarity and less acceptance by end users. Devices in this category include U.S. Pat. Nos. 4,507,117 and B1 4,507,117 to Vining et. al., 4,675,005 to DeLuccia and 4,747,830 to Gloyer. The reissued Vining patent provides means for repetitively and selectively locking and unlocking the needle to the plunger piston during use. Requiring the needle base to be locked into the plunger could add additional unnecessary burdens which may hinder ease of operation as well as teaching the correct use of the syringe. Locking the needle portion to the barrel portion is a worthy pursuit but should emphasize the use of standard parts and commercially available needles.

This inventor has provided the dual capability of use as a conventional syringe with a front mounting luer-lock fitting, should a user have a special need for such mounting. The term luer denotes the attachment of a needle to a syringe tip and is coined in honor of the nineteenth century German instrument maker. A glass syringe with airtight glass piston is called a Luer syringe. Luer-lock is a term used to denote the attachment of the female receiving cavity of a standard truncated conical hypodermic needle with ovate flange to the corresponding male fitment and threaded collar of a syringe barrel. If a threaded collar is not present, the syringe is then said to have a luer-slip tip. The instant invention also provides an internal luer-lock inside the syringe tip. In this case, the male fitment is formed on the tip of the plunger piston and a seal is formed along the outside smooth portion of the standard needle when it is mounted and integrated into the syringe tip.

Several methods of forming industrial seal are well known to the automotive, aerospace or pipe fitting industry. Several well accepted joint fittings include:
 (1) Threaded taper seal
 (2) Gasket or crush plate seal
 (3) O-ring seal.

Redundancy or combinations of the above are often provided when a reliable seal between joints is of critical importance. However, redundancy in itself is often a sing of poor understanding of stress factors that play upon the joint. For example, aerospace engineers utilize redundant O-rings in joints of booster rockets. The theory is that should the first O-ring be degraded and fail causing escape of hot gases and head, the back up O-ring provides a safety cushion to prevent a catastrophy. This approach may indeed provide appropriate protection but can never be totally reliable. This is because redundant O-rings, in themselves, are not configured to meet the challenge borne by tremendous internal pressures that develop during launch. Environmental factors such as low temperatures can compound problems and perturb inadequacies in unreliable seals. A reliable approach should take advantage and reflect appreciation of the large mass of each booster section and apply that mass directly to the joint and O-ring or rings. Therefore, a taper fit combined with one or more O-rings would provide the reliability and quality assurance that has been lacking in the past in this critical area of the space technology field.

A sealing means is also of critical importance between a needle and syringe. An externally mounted needle is adequately sealed in a luer-slip or luer-lock tip syringe in most instances. In normal use, pressure within the syringe does not build up extraordinarily. However, should a syringe piston be quickly depressed, a needle mayfly off the tip like a missle. An internally mounted needle is urged to become integrated with the syringe tip. A proper seal is of critical importance. A standard needle has a smooth tapered truncated conical hub or base section near an ovate flange. A matching taper or plastic O-ring integrated distal to luer-lock threads will allow a superb seal using a standard needle and can be provided at no additional cost to the manufacturer. Mechanical function requires that any seal between joints be equal to or superior to the wall strength between joints, under all working conditions and in all environments where a task is performed. By mounting a needle within a syringe barrel tip so that the needle base becomes integrated with the barrel tip, a superior seal which in and of itself, advances knowledge in the field, is thereby acquired.

By providing an outside luer, a second needle may shield a primary needle inside or a second catheter sheath could be passed off the tip as the needle is retracted inside the barrel. The term hypodermic syringe denotes a small syringe armed with a hollow needle for use in giving remedies by the subcutaneous method.

It is desirable to be able to both retract a needle into the syringe barrel and thereafter make the syringe unreusable. In addition, it is desirable that, when a plunger of the syringe is completely depressed, the grommet making up or surrounding the needle mounting hub is compressed which results in very little or no air remaining in the interior of the syringe and when the plunger piston is released, will spring back or rebound from the needle mounted internally in the barrel collar to facilitate self-aspiration of fluid while providing easy release from the needle base. This helps to insure that air can be vented from the barrel and replaced with liquid.

A device of this type is useful not only as a syringe for delivering or withdrawing fluids from a patient, but is also used in conjunction with a modified syringe barrel known as a needle holder-dropper device for the purpose of drawing blood. Arterial or venous catheter placement capability has been noted. A spinal tap apparatus, dental syringe or any similar device having a needle may be provided in order to protect the health care provider from needle-stick injury during or after use. The term dental syringe is used to denote a breach-loading metal cartridge syringe into which fits a hermetically sealed glass cartridge containing an anesthetic solution. The sealed glass cartridge consists of a glass barrel with a plunger grommet at one end and a sheet metal cap which is open and covers a rubber disk and is crimped over the opposite end. The glass cartridge may form the packaging for providing a syringe upon addition of a plunger piston and cap-needle mounting means.

A needle containing device is most dangerous at the time a task is being performed with it. Caps are prone to be lost or fall off and exposed needles then become a hazard to handlers and bystanders alike. Even a retractable syringe, if filled with blood or other fluid, has an exposed and potentially dangerous needle. U.S. Pat. No. 4,795,443 issued Jan. 3, 1989 is for a stick protector that clips onto a syringe barrel and can be guided over an exposed needle. However, such a device could be made even simpler and less expensive if the stick used rings to attach to the syringe barrel and standard cap that is provided along with a standard needle.

Glass ampules are widely used in the delivery of medicine. A glass top has a constriction point which is broken to allow access to the liquid or powder inside the ampule. Such delivery is associated with the possibility that shards or splinters of glass which may fall into the vial during breakage of the top may subsequently be aspirated unknowingly with the medicament. Vented needles have been developed to prevent coring of rubber should a vial have a rubber stopper that is penetrated by a needle. Such needles are expensive. Elaborate filter means such as straws have been developed to address the glass splintering problem. All alternatives are expensive and inconvenient. Therefore, a cost effective method of converting a cartridge ampule or other glass containment means into a syringe and keep the medicament separate from the needle until the time of use would be desirable if cost effective and provided the needle penetrate any rubber seal or disk in non-coring fashion. A machined light socket ferrule of appropriate configuration can be integrated into the tip of a glass syringe barrel and a male fitment included on a glass plunger piston to provide a retractable glass syringe with internal bayonette attachment for a retractable needle base.

This invention relates generally to disposable hypodermic syringes and more particularly to pre-loaded devices of this type employing a special pre-mounted needle adapted to pierce a sealing membrane or the syringe body of a syringe glass containment means, thereby rendering the syringe or cartridge operable. The sealing membrane is pierced so that coring of the membrane is avoided.

U.S. Pat. No. 3,825,003 to Kruck teaches precise and accurate control of the needle movement, especially with respect to penetration of the seal of a syringe body or cartridge. In this needle and cap assembly, the non contaminating cover is easily and quickly removed wherein a double pointed needle pierces the membrane. A needle lock is constituted of ears on the needle and cooperably locking shoulders on a sealing type cover. The cover, by means of its shoulders, holds captive a needle hub so as to releasably hold the needle in its advanced position against spring action. Upon turning the cover slightly, the shoulders thereof disengage the ears of the needle hub and the needle snaps to its retracted position so as to pierce the membrane to enable discharge of the product to be effected. Such a needle requires special tooling and equipment to incorporate a biasing spring in its structure. The number of parts required to make the hub of the needle rather large and, thus, impractical for use with a small syringe barrel or cartridge cap. In British Patent Specification number 1,489,813 and U.S. Pat. No. 3,974,832 to Kruck are found the teaching that in prior devices, where the hub and needle were free to turn as the latter pierced a sealing membrane, there was the danger that small pieces of membrane would tear off as the needle point axially rotated during passage. These pieces, if drawn into the hollow needle and injected into a patient, would have serious consequences. If screw threads were used, they must be "started properly" to prevent binding or damage and malfunction. According to the present invention, there is provided a needle and special coaxial mounting cap-needle assembly for a hypodermic syringe which provides a manual method of mounting a needle which, by eliminating the spring, makes the overall structure more affordable. The structure includes a needle having at least a point at one end for piercing the pierceable membrane of a syringe and a key, threaded member or a fastener made up of a hub intermediate the needle ends and having as a keying portion a standard needle base with a threaded portion or fastening means to adapt to a round or alternate eye opening cap of a syringe cartridge; or a modified eye cap with a mateable key opening corresponding in size and shape to the flange or shoulders of the needle assembly support base. In each case, it is important that the needle not be allowed to rotate as it passes through the sealing membrane and allowed to rotate or otherwise act on the eye opening of the eye cap only after full penetration and passage through the sealing membrane in order to prevent coring. It is noted that coring is not as great a concern with small diameter needles or soft sealing membranes.

Several devices, notably U.S. Pat. Nos. 4,710,170 to Haber and 4,592,744 to Jagger must be partially disassembled to be rendered safe. Disassembly is time consuming and confusing for users. Jagger points out in a New England Journal of Medicine article in August 1988, that the risk of injury depends upon the type of device used and that devices requiring disassembly have the highest risk. She investigated 326 needle-stick injuries in over a 10 month period and found that 17% occurred before or during use of the devices and 13% during or after disposal of the devices. Because of shortcomings in structural features, there is still an incentive for the worker to recap the device. The single largest cause of injury is due to recapping. In the Jagger study, workers missed the cap and stuck themselves when attempting to cover a used needle in 17.8% of the injuries. Needles piercing caps during recapping after use accounted for 10.7% while needles protruding from trash accounted for 8.9%. OSHA statistics suggest that over two million workers are at risk in hospitals alone. It is apparent that needle boxes are often not within easy reach. There may be one box on a ward or floor, usually located at the nurse's or aid's station. The distance from where the needle is used and should be disposed can be substantial, making disposal inconvenient. Additionally, the disassembled components are often contaminated, which detracted from the objective of disassembly and encourages recapping of the needle.

One of the primary shortcomings of many existing retracting needles is that each requires use of a non-standard needle support structure. As seen in the Vining patent previously mentioned, this means providing a needle with a base that has to be specially manufactured as opposed to using standard parts. When standard components are utilized, familiarity among users is retained and parts are interchangeable. Lack of familiarity increases the likelihood of misuse and increases the frequency of accidents.

U.S. Pat. Nos. 2,880,725 to Kendall teaches that a needle can be mounted from the inside of a cartridge or glass syringe barrel. This structure, while having features of interest, requires that the barrel opening be modified so as to receive and anchor the needle by a pawl mechanism. With the needle so anchored, it cannot be returned to a retracted position. Protection of the needle point is not possible after needle use. Also, U.S. Pat. No. 4,735,311 to Lowe teaches that insertion of a needle into a cartridge eye cap can be accomplished. However, no provision is given to prevent coring of the cartridge membrane or to lock the needle base into the eye opening of the eye cap.

U.S. Pat. No. 4,781,683 to Wozniak et. al. shows self-annulling syringes that cannot be shared or reused. However, there is no control over exposure of the injectant to the hydraulic expansion plug which is positioned in the outflow channel of the syringe. The instant invention eliminates such a problem by virtue of exposure prevention until the needle is retracted. A filter plug in the plunger piston barrel of the present invention allows a venting mechanism for gas while preventing passage of a liquid. This would be desirable for blood gas analysis as well as syringe pump medication delivery where gas such as $CO_2$ is produced and should be removed.

U.S. Pat. No. 4,735,311 to Lowe et. al. teaches a needle shield assembly for detachably mounting the shield hub or eye cap of a syringe. The shield is connected by a two step snap fit in which rotation of the shield cannot be prevented and therefore, coring is possible. The needle is unified with the plastic base. In the present invention, the base or cap ferrule of the cap might be independently removed leaving the central cap to protect the needle. Alternately, both parts may be removed together to leave the needle behind and fastened to the eye cap.

Interchangeable parts and molds provide that only slight modifications of existing parts or molds can accomplish the objectives of quality, performance and integrity of a new product structure. Retaining conventionally accepted mechanisms and parts when possible helps minimize training time and device costs and assures easy assimilation into a use environment.

The contributions of this invention are readily applicable to altered cartridges, or pre-manufactured cartridge-needles that are retractable, or a cartridge used to obtain a blood sample, or a cartridge that is manually mounted with a needle prior to syringe loading and allowing access to a fluid therein if so desired.

Two part syringes for the injection of medicaments are well known wherein two sub-assemblies are threadedly connected to one another prior to use of the syringe. Prior art examples include U.S. Pat. Nos. 2,778,359 to Friedman; 4,33,457 to Margulies; and 4,642,103 issued Feb. 10, 1987 to Gettig. In these syringe assemblies, one sub-assembly comprises a plunger rod slidably supporting a head member that is, in turn, provided with either external or internal threads. This threaded member is adapted to engage mating threads formed adjacent to the rear end of the syringe barrel or cartridge.

The present invention includes structure that corrects for the shortcomings of such prior art. Included herewith is an interlocked injector assembly for use with a conventional or retractable glass barrel with standard or modified eye cap. The firm interlock of the two subassemblies is achieved through the interaction of a twin lead threaded connector with opposing detents consisting of bumps, ramps or dimples between threads adapted to slidably surround the glass cartridge barrel and a second connector element housing the slidable plunger rod having two surface, strategically placed, corresponding bump or ramps 180 degrees apart which mate with the bumps between threads of the hub connector. As the bumps slide past each other, a resilient or compressible collet ring as part of the first connector element surrounding the glass barrel of a cartridge is axially compressed and locked into position to firmly secure the two interlocking connector elements and compressing the smooth external surface of the cartridge barrel wall. The same tip mechanism is duplicated in the example of the syringe gun injector assembly as well as the tip protected biopsy needle and breast marking system. This mechanism may also be applied to screw caps and containers generally used in the general packaging industry to assure seal integrity during shipment or during vacation or business travel by providing tactile reassurance of a seal being formed and the cap secured during single or repetitive use.

Pre-mounted cartridge needles have shortcomings whereby it is undesirable to expose the metal in the needle base to some agents prior to use. Rubber or other poorly secured needle caps encourage leakage or possible needle-stick injury when needles penetrate sidewalls. A rod contained in the base of the cap parallel to the sidewalls may alleviate this problem. A rigid cap that is capable of forming an airtight seal with the base of the needle may prevent fluid entry. Such a close fitting cap and cartridge could be loaded in combination into a dental syringe holder. Needles may be encapsulated after use by being made to retract into the glass containment means after use is complete.

SUMMARY OF THE INVENTION

The present invention is usable in conjunction with a syringe, cartridges, needle holder and dropper device, arterial or venous catheter placement unit, slide wing needle device, needle mounting encapsulator, or other medical apparatus wherein a needle device is utilized to hypodermically inject or withdraw fluid, or monitor blood pressure or oxygen content of blood for use in a syringe pump device. A syringe is provided that includes a syringe barrel or cylinder surrounding and axially slidable and rotatable plunger which may pass a guide wire and having an needle mounting hub positioned on the fluid engaging end thereof. The syringe barrel also has a needle receiving end including an internal luer-lock fitting. A bump or ramp placed between threads can signal that the needle or threaded cap means is secure and sealed. An incomplete groove in the side wall of the barrel might be substituted for the luer-lock or a partial system of shelves and bumps may perform the task of securing and/or retracting a conventional needle hub with flange.

A conventional needle having a support base that interferingly fits over the hub of the plunger piston is received within the syringe barrel and is secured in the luer-lock or alternate fitting at the end of the syringe barrel by depression and rotation of the plunger. The needle support base includes a connector suitable for being received in the female receiving cavity of the needle base.

In the general packaging industry, a screw cap may be provided with bumps between threads to interlock with corresponding bumps or depressions or as part of the thread shelf to better secure the cap to the bottle or otherwise provide a tactile signal to the user that the cap is reliably sealed and secured. In the present invention, this connector is preferably a radially extending flange as in a standard needle base or the collar cap and collet and threaded portion of an injector assembly.

In order to use the needle in a retractable syringe barrel, the plunger is depressed and the needle is extended through the tip of the syringe barrel or needle retaining shell as in a catheter placement unit, such that the needle support base engages the tip of the syringe barrel or barrel shell. The plunger is then rotated in the syringe such that the male luer ovate flange is threaded into the female luer-lock and past the pumps between threads so as to effectively lock the needle in position and form a taper and O-ring seal relative to the syringe barrel tip. Alternatively, a needle may be mounted in a very small syringe barrel by incorporating an interrupted groove in each opposing sidewall of the barrel so that the ovate flange extension of a conventional needle might be received in each groove simultaneously upon a quarter rotation of the needle base by the plunger piston. A modified light socket ferrule inserted in the open tip of a glass syringe could provide such a mount in a luer type syringe. Once the needle is mounted the plunger is then withdrawn without rotation and the hub is frictionally disengaged from the needle support base. The plunger O-ring grommet may be formed to initiate this disengagement by the resilient rebound effect of the grommet. This will initiate fluid aspiration. A catheter or another needle may be passed off the outside needle mount or, from the needle base, if a short nose syringe is used. The inside needle may be retracted by reversal of the process. A small syringe might have an oval opening whereby a non-standard needle base could partially pass through and rotate ¼ turn to a locked position. A cartridge eye cap may also accommodate such a needle.

Catheter placement units are designed to provide that the used needle becomes irreversibly fixed within the containment means. This can be effected by use of detents or groove in the needle hub which interlocks with a retaining bead or corresponding detents in the containment means.

The vacuum tube phlebotomy assembly is the most common device used for sampling blood. Current methods require screwing a needle in and out of a reusable holder. This provides an ongoing incentive for the worker to recap a used needle prior to disposal. An alternative needle holder and dropper device for use in obtaining blood samples through a hallway opening is formed. Sidewalls made thin along the axis of partial slits will facilitate use. The syringe barrel is modified to include the partial sectioning through or along the axis of the barrel. The slits may contain a clasp mechanism. Finger depressions may be added in the sidewalls to increase comfort or for applying pressure to the sidewalls to effect release or mounting of a needle. A needle encapsulation device provides an alternate method to mount the double beveled needle from within the barrel of the hallway holder-dropper. The needle is mounted such that its bevel is always up within the plane formed by the slots and mounting tip.

The slide wing intravenous infusion of blood drawing device is often referred to as a "butterfly." It is either attached to intravenous tubing for infusion of fluids or is adapted to syringes for drawing blood. It must be disassembled after use, and flexible tubing makes the handling awkward. Health care workers are injured attempting to dispose of dangling exposed an contaminated needles.

Heavy duty needles for biopsy purposes are reused many times during their useful hospital product life. Examples includes cardiovascular and radiology special procedure needles, soft tissue biopsy needles, bone marrow biopsy needles and needles used for anesthesia. The sharp points of such needles are always exposed and a potential hazard for healthcare and house keeping personnel. The instant invention provides for partial disassembly of the hub of such needles so that a slidable hub collet combination may track the shaft of the needle to be fixed in position along the shaft for marking purposes or to cover the exposed point prior to or after use of the needle is complete and to thereby protect the point and personnel.

The present invention is usable in conjunction with a syringe, syringe assembly or syringe gun, cartridge needle or cartridge, or other medical apparatus wherein a needle is utilized to hypodermically inject fluid into, or withdraw fluid from a patient or medical apparatus. For example, a syringe is provided that includes a syringe barrel or cylinder which can be loaded from behind after the barrel is swung open on pivots, or loaded from the side by putting a cartridge or cartridge-needle combination through a lost in the barrel. This dental syringe holder surrounds an axially slidable and rotatable plunger having a mounting hub positioned on the cartridge engaging end thereof. The mounting hub can receive a harpoon fitment for use with cartridges which are not provided with a threaded male piece for mating with the mounting hub. The syringe barrel also has a needle receiving end including an internal female threaded connection having slots or grooves at right angles to the threads for receiving corresponding needle hubs mounted from behind by a plunger mounting hub. The female threaded connection is provided for receiving a male mounted hub for use when conventional dental needles are mounted. A special syringe barrel shell accessory with internal runners of fins and detents is provided or protect the user or patient in case of breakage of a cartridge and to house the cartridge and/or needle when use is completed. The barrel shell might house a double pointed needle before and after use by placing notches in the runners or fins which receive the needle hub. The needle is then mounted by a mounting hub on the plunger piston and received at the end of use by reversing the process when the cartridge is first removed.

A needle with ridges on its base fits within the dental syringe barrel tip to corresponding slots within the tip. A small diameter cap over the long portion of the needle allows the needle to be mounted from behind by being able to pass through the syringe barrel open tip while still covered. Needles may also be mourned manually to a dental syringe or to cartridge and eye cap by use of a coaxial mounting cap. Such caps consist of three parts:

(1) A primary cap portion with external runners covering a portion of the outside base of the cap. This central cap may have an internal wrench capability formed by internal fins that cooperate with the base structure of a standard needle to signal a snap friction fit or to provide a needle with an airtight seal.

(2) A secondary cap ferrule which has runners or splines along the inside wall of the ferrule which fit within the outside runners of the central cap to form a spline system. Alternately, the function of the splines may be performed by a square, hex or star shaped opening in the top of the ferrule to correspond to the shape of the central cap base above its bottom edge or apron. A groove or bead may be provided in the ferrule opening to provide a snap interlocking means with the center cap prior to cap use.

(3) A third end cap which fits into the cap ferrule at its other end opposite the center cap opening. The cap-needle may otherwise be assembled and pre-mounted to the eye cap of a dental cartridge or syringe glass containment means.

The joining as disclosed is done for convenience and does not preclude other possibilities. Prior to use, each joint may be paper wrapped or heat detented and sealed to provide for needle sterility prior to use.

A needle is mounted to a sealed syringe body or eye cap of a cartridge by first being adapted to the outside edge of the eye cap. Several possibilities are disclosed for subsequently fastening an needle to the eye opening of the eye cap. All involve an interference fit inside the eye opening. In some cases, the needle may be mounted from inside the cartridge by machine. The needle may subsequently be adapted to the plunger or grommet of the cartridge where upon it is passed back through the eye opening to a retracted position inside the barrel of the cartridge for safe disposal. In other cases, the needle is mounted manually from the outside by using a coaxial mounting cap and fastening the needle inside the eye opening at the time of use. The conventional eye cap or a key structure or other structure modification may be used.

Once a needle is mounted to a glass or other containment means, an auxillary cap or modified center cap of a coaxial mounting cap can be used to house a second cartridge to allow transfer of materials from one cartridge to another at the time of use or otherwise allow for segregation of materials within each separate cartridge at the time of use. It is envisioned that such a system could keep cartridges and needles encapsulated and protected throughout the mixing process.

In another embodiment of the dental syringe barrel, a double beveled needle can be mounted into a threaded tip which contains a slit to allow the needle to simply drop out when the barrel is squeezed after use. The tip and barrel opens along the slit. Reversing the steps, the needle can be easily attached within the tip. A cartridge could be inserted and if evacuated, would be capable of collecting blood in the same manner that conventional rubber top tubes are used. In such case, a retaining wheel attached to the cartridge grommet would be useful.

OBJECTS OF THE INVENTION

A first object of the invention is to substantially improve protectable hypodermic needle devices and their accessories including syringes, cartridges, cartridge assemblies, dental syringes and assemblies, biopsy needles, needle holder-droppers, and coaxial cap-needle mounting assemblies.

A second object of the invention is to substantially improve retractable syringes by forming a retractable syringe that will work with commercially available hypodermic needles, will initiate aspiration of materials after the needle is mounted in the tip by including a resilient rebound boot as part of the plunger piston grommet, will secure and provide a reliable seal for such needles when mounted and will become irreversible after the needle is retracted by either breaking off the plunger piston or including a self-annulling plug in the syringe tip.

Another object is to provide a retractable syringe or catheter placement unit such that a guide wire may pass through the plunger piston or filter plug or extension included in the plunger piston bore to allow passage of gas but not liquid.

Another object is to form alternative needle bases for needle protectable devices that assist in mounting, securing, providing signals of blood vessel entry, retracting or otherwise helping to protect the points of such needles.

It is an object of the present invention to provide a gauged biopsy needle with a compound hub used to determine the depth of the needle point during use and protect the point following use.

It is an object to provide an improved slide-wing infusion and catheter blood drawing device in which the needle point may be protected by the wing housing and hub after use of the device is complete.

Another object of the invention is to provide improved syringe gun and cartridge assemblies allowing for increased ease and convenience in mounting and securing cartridges to such assemblies and removing cartridges and protecting needles after use is complete.

Another object of the invention is to provide methods of attracting a needle from behind the eye opening of an eye cap of a cartridge or syringe glass containment means prior to filling with medication. It is an object to propose means of fastening such needle bases to within the eye opening of the eye cap for subsequent retracting into the glass barrel after use is complete.

Another object of the present invention is to provide for usage of commercially available needles and conventional usage where possible so that a smooth transition can be made from old ways to new ways of providing protection.

It is another object of the present invention to provide a dental syringe or holder-dropper capable of making a cartridge self-aspirating, allowing a cartridge-needle combination to be loaded and providing for needle protection after use is complete. A cap handle is provided for safely recapping an exposed needle in a holder-dropper, dental syringe or other syringe or syringe assembly.

It is another object of the present invention to provide an improved method of mounting a double beveled needle to the eye cap of a glass cartridge or syringe wherein a two stage cap consisting of a center needle cover cap and a cap ferrule harnessed in tandem are mounted to the eye cap and eye opening of a glass containment means. This allows for attachment and segregation of needle and package contents prior to use. The needle is then manually fastened within the eye opening of the eye cap at the time of use by pushing the center cap and needle for attachment.

Another object of the invention is to provide cartridge tube devices for segregating and mixing cartridge contents in non-coring fashion and to provide for needle encapsulation and protection in the event that the cartridge is broken during use.

It is another object of the invention to provide detachable needle assemblies for an evacuated blood collection system wherein a container holder can be quickly and easily mounted with a double beveled blood drawing needle with bevel oriented upward by use of a clamp mechanism. By squeezing the walls of the holder-dropper, pressure causes the holder-dropper to open for mounting or releasing a needle. A cone shaped receptacle is provided for proper disposal of needles and syringes. A retaining wheel mounted to a cartridge grommet will allow a cartridge to be used a blood drawing tube when evacuated. A pediatric sized holder-dropper would be provided.

Other and further objects of the invention will appear in the course of the following description thereof.

DESCRIPTION OF THE DRAWINGS

The drawings are to be read in conjunction with and as part of the specification. Numerals are used to indicate like parts of the invention as shown in the various views.

FIG. 1 is a longitudinal sectional view from the side of a dual mounting, self-aspirating and annulling, needle retractable and irreversible hypodermic syringe and catheter placement device according to the invention.

FIG. 2 is a perspective view of a dual mount, irreversible and retractable piston type syringe showing an internally mounted needle.

FIG. 3 is a longitudinal sectional view of a dual mount retractable hypodermic syringe with plunger piston broken to render the syringe irreversible.

FIG. 4 is a cross-sectional view along line 4—4 of FIG. 1 and teaches the locking and securing mechanism for the commercially available standard needle.

FIG. 5 is a longitudinal sectional view taken along line 5—5 of FIG. 1 in the direction of the arrows.

FIG. 6 is an alternate longitudinal view in section taken along line 6—6 of FIG. 1 in the direction of the arrows.

FIG. 7 is a longitudinal sectional view from above of a front portion of a retractable catheter placement unit apparatus showing the needle base with forward flash back window, catheter, vent tube tip structure and finger ring accessory.

FIG. 8 is a cross-sectional view taken along line 8—8 of FIG. 7 showing where the needle base passes through the barrel shell safety shield for positioning of the flash back window.

FIG. 9 is a longitudinal sectional view of a front portion of a retractable winged catheter placement unit device with finger rings and a tracking wire.

FIG. 10 is an alternate cross-sectional view drawn at line 10—10 of FIG. 9 showing a hex shaped passage through the barrel shell safety shield for passage of the corresponding flash back window of the needle base.

FIG. 11 is a longitudinal sectional view of an alternate back portion of a catheter placement unit vent tube with sealing thumb ring attached and the back portion of a guide wire assembly contained therein.

FIG. 12 is a longitudinal sectional view of a back portion of a catheter placement unit device showing the back portion of a vent tube within a barrel shell safety shield.

FIG. 13 is a longitudinal sectional view of a guide wire assembly for a catheter placement unit.

FIG. 14 is a longitudinal sectional view of a retracted needle of a catheter placement unit within a barrel shell safety shield.

FIG. 14A is a perspective of a catheter placement unit device held by finger and thumb rings prior to needle insertion and catheter placement.

FIG. 15 is a longitudinal sectional view of a biopsy needle and needle bore rod apparatus with needle hub components spread apart.

FIG. 16 is a longitudinal view of a biopsy needle and hub components with rod replaced by a guide wire.

FIG. 17 is a longitudinal view of a biopsy needle and rod apparatus with needle tip protected and covered.

FIG. 18 is a perspective view of a biopsy needle as may be used for breast marking purposes.

FIG. 19 is a top overhead view of a slide wing vascular access apparatus with a catheter extension.

FIG. 20 is a top perspective view of a slide wing vascular access device with wing fixed to the tubing hub piece so that the needle is covered and protected and the slide wall is fastened to the tubing tail about the needle base.

FIG. 21 is a top longitudinal view of a cartridge ampule syringe assembly device showing collet and bump locking means between threads and finger and thumb rings.

FIG. 22 is a longitudinal sectional view of the cartridge ampule syringe assembly as shown in FIG. 21 in a locked position.

FIG. 23 is a longitudinal view of an alternate cartridge ampule syringe assembly with a dual bead retaining and locking means.

FIG. 24 is a longitudinal sectional view of the cartridge ampule syringe assembly with dual bead retaining and locking means of FIG. 23 in mounted position with collet clamped to the cartridge ampule.

FIG. 25 is a side view of an alternate syringe gun assembly with threaded bump or ramp lock tip and collet clamping means.

FIG. 26 is a top view of the bump or ramp lock and collet syringe assembly of FIG. 21 with cartridge ampule with a retracted needle shown.

FIG. 27 is a longitudinal sectional view of a glass containment means and rear mounted retractable needle means.

FIG. 28 is a longitudinal sectional view of a syringe or cartridge ampule end and alternate rear mounted retractable needle means.

FIG. 29 is a longitudinal sectional view of a cartridge ampule containment means and a rear mounted retractable needle means.

FIG. 30 is a longitudinal sectional view of a glass cartridge ampule or glass syringe tip and a rear mounted retractable needle hub means, rear mounting grommet and air tight sealing cap.

FIG. 31 is a longitudinal sectional view of a standard cartridge ampule or glass syringe tip and front mounted retractable needle means.

FIG. 32 is a front end view of a standard eye cap and eye opening of a standard glass containment tip means mounted with the retractable needle of FIG. 30.

FIG. 33 is a front end view of an alternate embodiment eye cap and key lock eye opening of a standard glass containment means with mounted retractable needle of FIG. 29.

FIG. 34 is a vertical sectional view of a non-coring coaxial mounting cap-needle assembly, eye cap and glass containment means with needle in pre-mounted position.

FIG. 35 is a vertical sectional view of a non-coring coaxial mounting cap-needle assembly, eye cap and glass containment means with needle fastened in mounted position.

FIG. 36 is a vertical sectional view of an alternate non-coring coaxial mounting cap-needle assembly, eye cap and glass containment means with alternate needle base in fastened and mounted position.

FIG. 37 is a cross-sectional view of a non-coring coaxial mounting cap-needle assembly taken at line 37 of FIG. 34.

FIG. 34A is a perspective view of an alternate non-coring coaxial mounting cap-needle featuring a hex shaped center cap base above the apron for sliding through the correspondingly shaped aperture in the cap ferrule.

FIG. 38 is a longitudinal view of a cartridge ampule grommet with male mounting fitment and plunger piston adapting means.

FIG. 39 is a longitudinal partial sectional view of a retractable self-aspirating dental syringe device.

FIG. 40 is a longitudinal sectional view of a retractable self-aspirating dental syringe needle mounting tip.

FIG. 41 is a longitudinal view of a retractable dental syringe accessory with self-aspirating stud feature.

FIG. 42 is a longitudinal view of a harpoon fitment accessory for a dental syringe plunger rod means.

FIG. 43 is a front cross-sectional view of the dental syringe tip taken at line 43 of FIG. 40.

FIG. 44 is a longitudinal view of an alternate embodiment center cap of a non-coring coaxial mounting cap-needle assembly for mixing medicaments.

FIG. 45 is a longitudinal view of a cartridge retaining means for mixing medicaments.

FIG. 46 is a longitudinal sectional view of a glass syringe tip metal ferrule for outside slip or rotational mounting and inside bayonette mounting of a standard hypodermic needle ovate flange.

FIG. 47 is a longitudinal top view of a pre-folded syringe or ring cap holder and safety recap handle for use with medical devices having unprotected needles during use and prior to disposal.

FIG. 48 is a longitudinal partial sectional view of a cartridge needle retaining shell for use with a dental or cartridge syringe and cartridge ampule.

FIG. 49 is a side elevational view of a retractable dental syringe showing removal of a cartridge ampule containing a retracted needle.

FIG. 50 is a side elevational view of a retractable dental syringe showing removal of a cartridge with externally mounted needle to cartridge and a cartridge shell cover of FIG. 48.

FIG. 51 is a side elevational view of a retractable dental syringe showing removal of a cartridge ampule. A self-aspirating retractable dental needle may be attached to the syringe tip.

FIG. 52 is a side sectional view of a dental needle with self-aspirating stud base and air tight center cap cover with cap ferrule removed and not shown for attachment to the syringe tip of FIG. 51.

FIG. 53 is a vertical elevational view of a needle holder-dropper blood drawing evacuated collection system showing thumb and index finger drawn in phantom lines.

FIG. 54 is a front end view of the needle holder-dropper blood drawing device of FIG. 53.

FIG. 55 is a vertical sectional view of the needle holder-dropper blood drawing device.

FIG. 56 is a front end view of the needle holder-dropper blood drawing device with needle mounting and dropping end open.

FIG. 57 is a vertical perspective view of the needle holder-dropper device dropping a needle through the hallway of the holder-dropper and into a truncated conical receiving containment means for disposal.

FIG. 58 is a vertical elevational view of an alternate needle holder-dropper device showing a modified cartridge ampule with retaining wheel for blood drawing use.

FIG. 59 is a vertical partial sectional view of a needle holder and mounting means encapsulating a double pointed needle with standard base fixtures reserved with respect to the needle extensions.

FIG. 60 is a top end view of the needle holder-mounting device taken at line 60 of FIG. 59.

FIGS 1-6, INCLUSIVE

Referring first to the improvements as shown in FIGS. 1-6, a syringe 10 capable of protecting a needle 22 after use, consists of a barrel 15 and a plunger piston 17 with a grommet 45. The barrel 10 is limited at its plunger piston receiving end by a finger flange 18 which extends perpendicularly from the axis of the barrel sufficiently to accommodate the index and middle fingers of the user. A retaining bead 21 is inside barrel 15 at the end encompassed by the finger flange 18. Progressing from the finger flange 18 along the outside of the syringe to the tip as shown in FIG. 1, one next encounters a constriction 19 followed by a section which contains an internal luer-lock housing 14 followed by another constriction 7 that is followed by a needle hub sheath portion 11. The needle hub sheath portion 11 has a constriction 6 at its forward end which is followed by a base 13 and an abutment 38 to a luer slip tip 12 which forms and limits the end of the syringe tip. A threaded collar means may be joined to the base 13 to convert the external luer-slip tip 12 to an external luer-lock tip. The sheath portion 11 may be sectioned along its length between constrictions 7 and 6 at a line 55 in order to provide the syringe tips of FIGS. 5 and 6. Needle base 23 may thereby be urged to function in place of the structures of the hub sheath 11, luer-slip tip 12, abutment 38 and base 13 when needle base 23 is mounted in a locked and sealed position.

Syringe barrel 15 provides for an internal chamber 16 which receives the plunger piston 17 for being mounted within and allowed to move axially and rotatably within said chamber 16. A construction 19 forms an internal funnel wall 3 which limits the extent of chamber 16 as well as forward movement of the plunger piston 17 and grommet 45. A retaining bead 21 is inside barrel 15 at the end encompassed by the finger flange 18. Progressing toward the syringe tip from the retaining bead 21, a plunger piston back plate recess 2 is followed by an intermediate step 1 in the internal chamber 16 for governing movement and breakage of the forward end of the plunger piston. The funnel wall 3 is followed by the internal luer-lock housing 14 which is limited by funnel wall 36. Funnel wall 36 also limits the forward movement of needle flange 25 to be described later. The funnel wall 36 turns into the inner chamber 4 of the needle hub sheath 11 where secondary needle seal bead 41 is located to form a back-up seal with the smooth portion of the needle base. The inner chamber 4 is then limited by funnel wall 37 which corresponds to the outside constriction 6 and a retainer bead 33 which limits backward movement of a self-annulling plug 32. The plug chamber 5 is next found which is limited by the interior abutment 39 forming the forward limiting means of the self-annulling plug 32. From the interior abutment 39, the syringe tip ends at the forward extension of the luer-slip chamber 20.

A commercially available standard hypodermic needle consists of an ovate flange 25 at the extreme end away from a needle 22. The ovate flange 25 is followed by a smooth base portion 23 housing a female receiving cavity 24. The smooth part of the needle base 23 is followed by a finned portion 27 about a collar 26 in which the needle 22 is inserted and joined. The standard ovate flange 25 at the extreme end of the needle base is used as a locking means into the internal luer-lock 30. This luer-lock 30 is made up of structure that provides groove 28, thread 29 and a detent means 31 between thread 29 and funnel wall 36. Ovate flange 25 of needle base 23 is received in grove 28 and is locked in place by passing by or over detent means 31 to come to rest in groove 28 beyond the detent means. In lieu of an internal luer lock, FIGS. 5 and 6 teach locking a needle in the tip of a syringe by providing key elements of the grooves, bumps or thread shelf of the luer-lock described above for FIG. 1. The short tip syringe in FIG. 5 provides a groove 28' in the side wall of the syringe which, with a corresponding partial groove in the opposite side wall, might receive and provide a tactile signal to the user as a standard ovate flange 25 of a needle base 23 is passed into the groove and the base locked and thereby urged to become a functional part of the syringe tip. Similarly, a thread shelf or shelf system 29' is provided in the syringe tip of FIG. 6 to receive an ovate flange 25 of a needle base 23. Bump or detent means 31' may provide a tactile signal or securing means as part of groove 28' or thread shelf 29' to provide the signal as the ovate flange 25 moves by and contacts the detent means while traveling toward its seated and mourned position. Cap 8 or alternate cap tip 9 may be provided to lug the short tip syringe to further protect the retracted needle 22 in the short tip model. An alternate ovate or key lock opening syringe tip would allow mounting of a corresponding needle base with use of a round flange. Systems which utilize non-standard syringe tips with corresponding needles and sealing means are described later with cartridge ampule syringes.

A self-annulling plug 32 formed of rubber or hydrophilic expansion material, is positioned around the needle 22 in front of the fins 27 of the mounted needle base 23. As shown in FIG. 1, the plug may be pre-positioned in the syringe tip within the luer-slip tip base 13 to provide a second back-up seal for the needle in order to prevent loss of medicament or liquid prior to use and a self-annulling seal when use is completed and the syringe is rendered inoperative after the needle is retracted. Once inserted, a retainer bead 33 prevents further displacement of the self-annulling plug 32 from within luer-slip tip 13.

Retraction of the needle is accomplished by the addition of a male fitment 34 at the needle capturing end of the plunger piston 17. The male fitment 34 has the shape of a truncated cone and frictionally engages with female receiving cavity 24 of the standard needle base 23. An alternate needle cannula fitment 22A, if provided, may be received in a corresponding female receiving pocket 34A within the male fitment 34 to allow separate detachment of the needle cannula 22 and fitment 22A from the needle base 23 and allow the cannula as fastened to the female receiving pocket 34A to be retracted after use is complete. The end of the fitment 22A may have a short bevel and point 22B which may be urged to puncture the rubber grommet or membrane of a conventional syringe or male fitment 34 when used therewith, and thereby break the vacuum sealing capability to render the syringe irreversible or otherwise communicate with the inside of the plunger piston. A sealing bead 35 circumferentially located along the length of male fitment 34 or adjacent the mounting pedestal 42 assures a mateable surface with the corresponding female receiving cavity of the needle base so that the needle can be secured and also retracted when desired. Such a contact means provides interference when the needle base is axially rotated during needle mounting and sealing and less surface area contact when easy release from a tip mounted needle is desirable for accuracy and comfort during aspiration of material during use.

In addition to constriction 19 at the at the end of syringe barrel 15, it is to be noted that internal luer housing 14 is joined to needle hub sheath 11 by a tapered constriction 7 having an inner surface or funnel wall 36 which forms the forward limiting means of groove 28 in luer-lock 30. The side of thread 29 which is adjacent to groove 28 forms the rearward limiting means which along with funnel wall 3, secures ovate flange 25 within the luer-lock detent means 31. The needle is securely anchored within the syringe tip by such internal luer-lock means and flange engagement therein. It is noted that a detent means between threads may be introduced in any screw threaded systems to provide a tactile signal of seal integrity. The hub sheath 11 is connected to the base of the luer-slip tip 13 by a tapered constriction 6 with the plug retaining bead 33 interiorly thereof. The luer-slip tip 12 is connected to its base 13 by an abutment 38 which provides an interior abutment 39. Such abutment 39 and retainer bead 33 and the interior surface of the base of the luer-slip tip 13 form plug chamber 5 and the self-annulling plug 32 is secured therein in operative position.

A secondary seal bead 41 is provided within needle hub sheath 11 as a secondary seal for needle base 23. This assures adequate sealing of the base of the needle 23 within hub sheath 11 in chamber 4. The primary needle base seal is provided by the taper of the sheath 11 against the smooth taper of needle base 23.

At the base of male fitment 34 of plunger 17 is formed the needle mounting pedestal 42 which is a flared portion with a step 43. The mounting pedestal may conform or move against the interior of the beginning of luer thread 29 or threads 29 if double lead threads are used. When the plunger piston is fully depressed, the pedestal may be shortened along with the length of the luer-lock housing 14, should the threads 29 begin at the end of funnel wall 3. A plunger face 44 is connected to the base of the pedestal 42 and is substantially dome shaped to conform with funnel wall 3 of barrel constriction 19. The grommet 45 is supported between plunger face 44 and a back plate 46 so as to form a sliding seal for the plunger as it moves within the chamber 16.

The shaft 47 of the plunger extends from the back plate 46 to a thumb plate 48. The shaft 47 is constructed with a central axial configuration with a plurality of fins 49 extending radially therefrom. The shaft might otherwise be tubular and hollow. The fins or tubular shaft is constricted into a breakable section 52. The shaft 47 has a second constriction 52 located in cooperation with the thumb plate 48 to be narrowed in such a manner as to enable increased comfort and full control by the user.

An optional addition to this embodiment is a catheter guide wire 56 with sealing hub 57 which can be removed leaving a channel 53 in the center of the plunger. This channel would pass through the entire plunger 17 and needle 22. A gradient filter means 58 permeable to air but not liquid could allow for venting of air and retaining of blood for use in determination of blood gas measurement or syringe pump device. A similar venting means is possible by addition of periferal grommet channels 59 placed longitudinally along the grommet surface. Other small holes punched in the face of the grommet could allow for air but not blood passage. Larger holes could cause the vacuum to fail a has been previously described. A catheter placed over the luer-slip tip 12 of this syringe embodiment would provide for arterial catheter placement.

FIG. 2 show the complete syringe described in FIG. 1 assembled so as to be ready to be filled with medicament or mounted with an arterial or venous catheter.

FIG. 3 shows the same syringe after having been used. The needle has been retracted into the barrel chamber 16, the plunger 17 has been broken at constriction 51. The syringe is not usable, the needle is safely confined and shielded and is ready for safe disposal. A self-annulling plug, if provided, will further render the syringe non-reversible because a new plunger and needle could core the annulling material and plug the needle prior to its use.

FIG. 4 shows a cross-section at line 4—4 of FIG. 1. Internal luer-lock 30 has detent means consisting of bumps or ramps 31 integral with its interior placed 180° degrees apart for double-lead threads. Grooves 28 and threads 29 are shown so as to indicate the means whereby the needle ovate flange 25 is received and consequently, where the needle base is then properly secured and integrated in the syringe tip.

The syringe shown in FIGS. 1-6 illustrate the principles of the invention. It is readily seen that structure is directed to utilizing commercially available needles, catheters and guide wires. The syringe needle is an "off the shelf," standard item as used in the conventional, unprotected syringe. The luer-slip tip 12 is equally adapted for the attachment of a catheter or another larger diameter needle. An outside luer-lock collar may be attached to abutment 38 or base 13 of the luer-slip tip to provide conventional syringe functions.

In one operation of the syringe as taught, the base of the needle female receiving cavity is engaged with the male fitment 34 on plunger piston 17. The needle is inserted through self-annulling plug 32 from the inside chamber 16 and through the luer-slip tip 12 to be mounted for use. Upon engagement with internal luer-lock 30, the ovate flange 25 is locked therein by rotation of the plunger 17 a quarter turn in order to pass the flange over and clear the detent means 31. Grommet 45 with its rebound boot 54 is compressed by such insertion to store energy that gives a kick-back to initiate separation of the male fitment from the needle base female receiving cavity 24. Should the needle be inserted into a bottle or vial of medicine or into a blood vessel during such compression of the grommet 45, fluid aspiration will be initiated by resilient rebound. The amount of fluid aspirated is limited by the back plate 46 making contact with retaining bead 21 at the end of chamber 16. An intermediate step 1 and back plate recess 2 may first be encountered by the back plate to signal this approach and to stabilize and break the plunger piston.

The fluid in the chamber 16 is delivered to the patient through the needle in the conventional way. When the dosage is fully administered, the grommet 45 and its rebound boot 54 are at once compressed and this time, the needle is captured by the plunger by the engagement of female receiving cavity 24 of the needle base by the retaining band 35 of the male fitment 34 to be unified and a quarter turn opposite from the locking direction will free the ovate flange 25 from the luer-lock to release the needle. The user can once again feel the flange pass over or by the detent means. The plunger is then retracted to pull the captured needle into the cavity 16 of barrel 15 as shown in FIG. 3. Any residual fluid inside the syringe would be exposed to the self-annulling plug 32 which responds by swelling to form a seal. Should the plug 32 be made of rubber, the rubber simply close to seal itself. The fully retracted needle and plunger male fitment are then hermetically sealed within the barrel 16 and bead 21 assures that the grommet and back plate 46 are securely retained. With the plunger fully retracted, the plunger that extends beyond the barrel is broken at breaking point 51 and discarded. The syringe is thereby rendered safe, self-contained, non-reversible with needle and retained residual infections waste presenting no danger to the community. This includes innocent bystanders. By the use of standard components that are readily adapted without the requirement of expensive modifications, quick acceptance is likely.

Attention is directed to the demarcation 55 in FIG. 1 which is along needle hub sheath 11. This indicates where the hub sheath may be sectioned to allow the needle hub and base 23 to be integrated with the syringe tip as shown in FIGS. 5 and 6. The needle and tip may be capped or a dual loop cap handle device may tether a cap to protect fingers if recapping is required during use of a syringe.

It is also to be seen that, in applications such as pulmonary arterial thermodilution balloon catheter techniques, this syringe without a needle, may be used in a flow-limited manner. Upon full entrainment of a volume of gas to inflate the balloon, a dead space that exists within the needle hub sheath 11, along with the space within tip 12 becomes a safety cushion during overinflation of a balloon in a narrowed vessel. This takes advantage of the knowledge that a gas or air can be compressed to a greater degree than can a liquid when confined in an empty space.

FIGS. 7-14A, INCLUSIVE

Referring now to improvements shown in FIGS. 7-14A, the catheter placement units shown are syringe modifications where a barrel shell safety shield 83 is provided in place of a syringe barrel 15 for encapsulating a needle for disposal after use is complete. FIGS. 7 and 9 show the front portion of a catheter placement unit 61. The single unit is shown in two figures so that the details can be set forth clearly. The catheter placement unit 61 includes a needle sheath 62, a catheter 63, and a needle 64 with its bevel 65 shown in an upright position, facing upward when a marker such as window 75 is seen to be upward indicating proper positioning of the bevel. A catheter hub 66 surrounds catheter 63 and has a sheath hub 67 for holding needle sheath 62 until use. Catheter hub 66 has a female receiving chamber 68 for engaging male fitment 69 of the needle 64. Additional securing means between the catheter and the needle could be accomplished by providing a sealing bead 71 inside the catheter hub 66 along the length of the female receiving chamber 68 to engage a corresponding groove 72 in the male fitment 69. Alternatively, the securing means may be interlocking beads. A flash chamber 73 is located at the interior end 74 of the needle 64 and receives the blood from the needle during vessel entry. This blood is readily visible in the flash chamber 73. This provides a signal or visual cue that vessel entry has been achieved. This chamber 73 can be oriented to a surface window 75 in a disk shaped or pocket 76 to accelerate the realization of the blood flash back. Window 75 can have an emblem which indicates that the bevel of the needle 65 is in an upward position with respect to the blood vessel to be entered.

Needle base 77 has an ellipsoidal or spindle shape which may be solid or finned. The spindle shape can be accomplished by having fins 78 which extend from a tubular core 79. The cross sectional configuration of the needle base 77 may be ovate in shape where the end engages the ovate opening 86 of end retaining means 85 of the barrel shell safety shield 83 so as to assure that the orientation of the needle bevel 65 is controlled since it is oriented the same as the window 75. The opening 86 may be any non-circular shape (square, hex, star, etc.) as could a self-annulling plug if used in this area so long as the needle base has a matching shape that prevents rotation of the safety shield with respect to the needle.

At a place where the diameter of base 77 is maximum, a cleft 81 is provided in the fins 78. Cleft 81 is the mating surface area to lock with a retaining bead 82, which is located on the inner surface of barrel shell safety shield 83, at a position that when said mating is accomplished after use of the device for catheter placement, the entire needle and its base are completely enclosed in the barrel shell safety shield 83. The base 77 is interior of the barrel shell safety shield 83 and can be moved between the limiting retaining means 85 and the position described above when the cleft 81 engages the retaining bead 82 ss shown in FIG. 14. The needle is secure and encapsulated for disposal.

FIGS. 8 and 10 show the ovate opening 86 in the end closure 85 and the section of needle base 77 that is correspondingly shaped to assure non-rotation of the needle. The flash chamber 73 is revealed so that presence of blood through window 75 is not obstructed form view.

In FIGS. 11 and 12, the safety shield 83 is of constant tubular dimension with the retaining means 85 at one end thereof, and an interior retaining means 87 at the opposite end. The second retaining means 87 is for sealing the end of shield 83 and for positioning the vent tube 84 therein. The vent tube 84 is tubular in shape and has male fitment 88 at one end distal from the luer attachment end for thumb ring 95. The male fitment 88 is provided with a bead or flange 89 to securely connect the male fitment 88 and the female receiving chamber 91 in the end of the needle spindle 77 that is distal from the needle bevel 65. A filter 93 is included to prevent loss of blood through the vent tube. The location of the filter is not critical so long as it is positioned to prevent loss of blood. Another filter 94 is positioned between the end of the male fitment 88 and the bottom of the female receiving chamber 91 in the needle base 77. The thumb ring 95 is secured to the end of vent tube 84 either by welding or by known luer-lock threading methods.

For venous catheter placement, a vent hole 96 is provided through the thumb ring 95 and is positioned to provide access to the atmosphere from the interior of the vent tube 84. In the operation of the venous catheter placement unit (CPU), the operator locates the vessel for placement. Upon removal of the device from the peel pouch as received from the manufacturer, the position of the bevel 65 is in an upward position as assured by the upward position of window 75. The vessel is entered by the needle and catheter together. Upon entry, a flash back of blood is visible at the flash chamber window 75. The catheter 63 is then pushed with fingers on the catheter hub 66 so that sealing bead 71 disengages with groove 72, and the catheter 63 is inserted in the vein of the patient with the needle 64 as a guide. When the catheter is fully inserted, the complete needle assembly, including needle 64, male fitment 69, and needle spindle 77, is retracted into safety shield 83 until the cleft 81 of spindle 77 engages retaining bead 82. When finger rings are used, opening the distance between the thumb and fingers retracts the needle mechanism to be completely encapsulated within the barrel shell safety shield. The opening to the female receiving chamber 91 could be broken by the vent tube if true irreversibility is desired. The needle base is secured by the engagement of the cleft 81 in the needle spindle 77 and the retaining speed 82 of the interior of the safety shield 83 as shown in FIG. 14. If needed, caps may be readily attached to the two ends of the barrel shell safety shield or self-annulling plug added within the shield opening to completely isolate the needle and residual material contained in the shield. The vent tube 84 and attached thumb ring 95 and finger rings 80 are removed from the unit by disengagement from the vent tube and barrel shell safety shield, respectively. The vent tube and encapsulated needle are discarded and the rings used again.

It is noted that the catheter placement unit (CPU) 61 is held by the user on the outer surface of the barrel shell safety shield 83 at the end which includes the end retaining means 85. The finger ring assembly 80 is attached surrounding safety shield 83 and abutting the annular end ring of retaining means 85. The rings 80 are mounted by sliding the signet ring connecting means over the safety shield 83 to a resting position against the abutment presented by the annular ring of retaining means 85.

The CPU shown in FIG. 9 is for arterial catheter placement. The needle spindle 77, the catheter hub 66, needle sheath 62, cleft 81, female receiving chamber 91, male fitment 88, safety shield 83, rings 80 are the same for all figures. The structure specific to the arterial placement unit are shown in FIGS. 9, 11, 12 and 13. A winged catheter hub means 97 is attached to the end of the catheter hub 66 distal to the needle spindle 77 to provide the normal function of a wing for fixation to skin after the catheter is inserted into a vessel. The open vent tube 84 is tubular and fits within the safety shield 83 while providing an inner chamber 98 to accommodate the activity of a plunger 99. The vent tube 84 has a male fitment 88 which fits into a female receiving chamber 91 for movement of the needle structure 77 and 64 into operative position before use and into disposal position after use as shown in FIG. 14. The vent tube 84 has detent means 92 as shown in FIG. 9, to position the needle spindle 77 in secure, solid condition for catheter placement. The detent means 92 is located in the vicinity of the luer attachment end of vent tube 84. As shown in FIGS. 11 and 13, thumb ring 95 has an arcuate sealing means 101 which fits with the surface defining the trailing open end of vent tube 84 to make a seal when the plunger 99 and guide wire is fully inserted. FIG. 13 shows the plunger and guide wire structure utilized in arterial catheter placement using FIGS. 9 and 11. FIG. 13 shows a guide wire 102 which extends from plunger 99 as shown in FIGS. 9, 11 and 13 to provide for guide wire use. Vent tube 84 provides for a channel in which the elongated flexible guide wire 102 can be inserted all the way through the placement structure to exit through the needle 64 as shown in FIG. 9 to guide the placement of the catheter 63 in an artery of the patient. The flexible guide wire 102 is inserted through the needle spindle 77 and needle 64 after entry into an artery. Wire 102 is then positioned to be a guide for the insertion of the catheter 63 into the artery. It is to be noted that the modified plunger is solid in cross section and that seal means 101 prevents flash back of any blood out of tube 84. The phantom line 103 in FIG. 9 and FIG. 13 is shown to illustrate that the guide wire is flexible.

In the operation of the arterial catheter placement unit shown in FIGS. 9, 11 and 13, needle 64 is passed into an artery of the patient. This entry is instantly detected by seeing blood in the flash chamber 73. The flexible guide wire 102 is directed into the artery by moving plunge 99 within the open vent tube 84. A seal is made by the hub of the thumb ring plugging the vent tube. The catheter hub 66 is grasped by the fingers and thumb of the free hand of the operator and separated from the needle spindle 77 and the catheter 63 is moved to the proper position in the artery. Wing 97 provides a surface whereby the catheter is secured to the skin of the patient to enable the catheter hub 66 to be available for connection of the fluid handling equipment. Note that a detent means, if provided on the male fitment of the tubing of the fluid handling means, would allow for a secure lock when inserted into the female receiving cavity of the catheter. Possibilities include a bead or groove circumscribed around the male fitment corresponding to the bead or detent means within the female receiving cavity. The guide wire is removed from the apparatus. The needle and hub is retracted into the safety shield 83 until the needle spindle cleft 81 engages bead 82 so that the needle is fully encapsulated and accidental dislodgement of the needle is prevented as shown by FIG. 14. Disposal of such guide wire would be by conventional methods and the shielded needle is also rendered irreversibly contained and no longer a threat.

Plunger 99 as shown in FIG. 13 could be reused since it is not exposed to blood in proper usage. The guide wire and female receiving hub 98 may be separated as shown in FIG. 13. The flexible guide wire 102 also facilitates the provision of a seal within the needle. Hub 98 may be used as a sealing means for the vent tube male fitment 88. The vent tube 84 and attached thumb ring 95 are removed from the unit by disengaging male fitment 88 and female receiving chamber 91. The vent tube is discarded as is the encapsulated needle in proper fashion.

FIGS. 15-20, DESCRIBED PROTECTED NEEDLES

Referring to FIGS. 15-20 inclusive, hypodermic needle points may be protected after use by sliding and stabilizing hub components or a winged housing over and about the needle point. What is shown in or focused on in FIGS. 15-18 inclusive, are various vies of a needle biopsy instrument 201. The biopsy instrument parts include a needle stylet and hub 202 consisting of a trocar pin 203 inserted into a threaded hub 204. Threaded hub 204 contains a threaded portion 217 followed by a collet clamping means 219 which consists of radially arranged keys 220. The trocar pin 203 passes through needle hub 205 and through needle shaft 206. Needle hub 205 may be fastened to stylet hub 204 by threaded means 211 of female receiving cavity 212. Needle hub 205 and female receiving cavity 212 may be replaced by a standard needle base and ovate flange if preferred. Threads may be double or single lead and a bump or ramp detent means between or as part of threads may be added to secure attachment between parts. The needle and trocar or needle shaft 206 by itself will next pass through needle collet hub 207 which is capable of being fastened to needle hub 205 by hub threads 213 of female receiving cavity 214. Threaded hub 205 may otherwise contain a threaded portion 221 turning into a collet clamping means 222 which consists of radially arranged keys 223. Needle collet hub 207, when not fastened to needle hub 205, is allowed to freely track or slide along needle shaft 206. Detent marks 208 may be provided along needle shaft 206 as a calibration means or site marking means for locating an internal or anatomical structure and as a depth gauging system when sued in conjunction with x ray or other imaging means. The needle collet hub 207 may next encounter sentinel hub 209 and threaded means 215 of female receiving cavity 216 of sentinel hub 209. Collect hub 207 contains a threaded portion 224 turning into a collet clamping means 225 consisting of radially disposed keys 226. Threaded stylet hub 204 with trocar pin 203 may be removed to allow passage of a guide wire 218 which would provide a pathway upon which a catheter device may be used to track the guide wire into the subcutaneous anatomical site of interest for subsequent medical procedure or treatment. Threads may be single or double lead and bumps between threads may be added to signal the user that hub pieces ar securely joined.

In the operation of the biopsy device, all hub pieces would be joined prior to insertion as shown in FIG. 16. Upon hypodermic insertion, the needle tip is guided to the location of interest within the body. The stylet hub 204 with trocar pin 203 are removed. The collet hub 207 and sentinel hub 209 are moved away from needle hub 205 and down the needle shaft 206 for gentle contact with the skin surface as shown in FIG. 18. Guide wire 18 may be inserted through the needle bore. Prior to guide wire insertion, a syringe might be joined to needle hub 205 in order to instill medicament or to aspirate fluid. Upon insertion of a guide wire, the needle cannula and hub assemblies may be withdrawn over the guide wire and removed. At this time, the position along the needle shaft of fixed hub collet 207 and sentinel hub 209 are documented. Hub collet 207 and sentinel hub 209 may then be positioned to cover the needle tip and the hub collect 207 secured to the needle shaft 206 by twisting to tighten the threads and keys of collect 207 and sentinel hub 209. With the needle tip so protected as shown in FIG. 17, the biopsy instrument is then ready for handling by other health care personnel such as Radiology, Anesthesiology, Nursing, Special Procedure of Pathology lab staff. Biopsy material may be better protected during transport for lab analysis if first collected in the needle and the hub pieces subsequently manipulated about the tip of the needle as described. The tip of the needle could be left guarded in this manner between uses after instrument sterilization is completed.

As previously stated, FIGS. 19 and 20 show top vies of a slide wing infusion device prior to and after use. The wing assembly 261 consists of a slide wing 265, catheter 264 and tail assembly 266 having capability of tracking or moving along the needle shaft 262 to protect the needle point 263 as shown in FIG. 20. The catheter end 264 is integrated with the soft pliable winged portion 265 containing wing holes 272. A trailing tail portion 266 with tail holes 273 extends from the back edge of the wings beneath the infusion tubing 267. The infusion tubing 267 terminates by joining the rear end of the needle shaft 262 and provides a wedged attachment means 268 containing detent prongs 274 in front and a truncated female luer attachment 269 at its opposite end. A cap may be provided to protect the luer attachment prior to use. Alternately, the luer attachment may be fitted to wing slots 271 after use is complete to further encapsulate a protected needle point as shown by FIGS. 19 and 20.

In use, one grips flexible wings 265 with thumb, index and middle fingers after removing a protective needle sheath 275 provided by the manufacturer as drawn in phantom lines in FIG. 19. The needle and winged catheter are used in the usual way. After the needle has been used, the wing is detached form the detent prongs 274 of wedges attachment means 268 by pulling prongs 274 from wing holes 722 so that the winged portion 265 and catheter end 264 may be moved along the needle shaft 262 to cover and protect the needle point 263. Tail portion 266 may then be attached to wedged attachment means 268 by fastening detent prongs 274 of wedged attachment means 268 into tail holes 273 of tail portion 266 as shown in FIG. 20. Truncated female receiving luer attachment 269 may be attached to wing slots 271 to further encapsulate and protect the needle prior to disposal.

While the embodiments to these figures have been described with specific reference to embodiments, modifications and variations, other possibilities may be constructed. For example, in lieu of threaded attachment for biopsy needle hub sections, a detent means using a spring and ball may provide for detachment and connection of separate pieces.

FIGS. 21-26 INCLUSIVE, DESCRIBE SYRINGE ASSEMBLIES

FIGS. 21-26 inclusive, show syringe and gun assemblies directed to protect needle encapsulation in devices that utilize medicament-laden cartridges. FIGS. 21-52 are directed to needle protection in devices such as dental syringes, glass containment syringes and holders and cartridge-needle units. The collet clamping and thread locking means of attachment is further utilized and described in the operation of the assemblies of FIGS. 21-26. FIG. 21 shows an injector assembly 301 which is formed of parts which include a nut 302 which slides over a collet 303. The nut has an interlocking threaded means 304 on its interior surface consisting of a bump or ramp 312, thread 306 and retension bead 309 as shown more clearly in FIG. 22. A barrel 305 is integral with the collet 303. The outer surface of barrel 305 has a surface thread 306 for engagement with projecting detent means 304. Collet 304 has radially disposed collet keys 307 which grasp a medicament cartridge 308. A closed bead 309 around barrel 305 acts to retain internal bead 311 of nut 302. Double lead threads 306 with corresponding double bumps or ramps 312 make contact with detent means 304 of nut 302 to allow for a screw securing means which is locked when nut 302 is turned a quarter rotation to mount and secure the nut and medicament cartridge within the collet. The dimensions of the detents and their radial positions are determined by the requirement of providing secure locking of the nut and the collet in the use position.

The collet 303 has at its end away from barrel 305 and threads 306 a plurality of collet keys 307 which grasp a medicament cartridge 308. Retention means 309 is provided which permits the nut 302 to be mounted and secured to barrel 305 at all times. Keys 307 secure the medicament cartridge 308 when the nut is in its locked position so that the injector assembly can be stabilized, that is, without movement between the barrel and the cartridge. Elastomeric band 313 may be provided between collet keys 307 and the cartridge side wall as a cushion between cartridge and collet keys. The barrel is provided with finger rings 314, a plunger 315 and a thumb ring 316. A chamber 317 is provided in barrel 305 to allow movement of the plunger axially within said barrel 305. Chamber 317 terminates internally in barrel 305 with an enlargement 318 that provides for female connector 319 at the end of the plunger opposite said thumb ring 316. A male connector 321 is integral with the sealing grommet 322 in the bottom of medicament cartridge 308. A male fitment 323 is located on the opposite face of the grommet 322 for use in mounting or retracting a cartridge-needle as shown in FIG. 26 and further in additional figures to be presented. The cartridge-needle might be any of the endless depicted in FIGS. 26-33 where needles are mounted within a glass containment means such as a cartridge or syringe barrel with a sheet metal cap covering a rubber disk or membrane or alternate needle sealing means. These needles may then be fully retracted into the containment means after use is complete to protect and encapsulate them after use is complete.

FIG. 22 shows the structure of FIG. 21 in longitudinal section along the center lien of the device. The nut 302 is shown in its secured or locked position at which time collet keys 307 are tightly holding the medicament cartridge 308.

FIG. 23 shows an alternate structure of the injector assembly with nut 331 and barrel 332. The assembly is operable in a clamping mode and then changed to the release mode simply by sliding the nut along the barrel and over closed bead 336. A collet 333 is integral with the barrel 332 and has keys 334 extending therefrom. Interior of the nut 331 is a closed band 335 positioned circumferentially near one end of the nut 331 as shown in FIG. 24. On the barrel 332 are a pair of closed beads 336 and 337 as shown in FIG. 23. A corresponding bead 338 which may be incomplete inside nut 331 first passes over bead 336 and then passed bead 337 to be limited by reversed finger flanges 339 of barrel 332, and the collet keys 334 are tightened by the nut to secure the cartridge 308 as the corresponding bead passes over the second closed bead 337. The resulting position is shown in FIG. 24. Therefore, the nut 331 is passed back and forth over the second closed bead 337 to both secure and release the cartridge 308 within the barrel 332. Bead 336 is shaped to allow the nut to pass over it with ease only during primary assembly while the closed bead 337 is beveled on the front and back edges so that the nut corresponding bead 338 may pass back and forth over it as desired during repetitive use. The nut 331 is always retained about barrel 332 being held between reverse flanges 339 and closed bead 336 and being allowed to slide over bead 337 to bring flange pairs 341 and 339 together in a locked position and then slide back over the bead 337 after medication from cartridge 308 is dispensed and flanges are apart for cartridge grommet detachment and cartridge removal from female connector 319 for disposal.

FIG. 25 shows a gun injector assembly 351 which is formed of parts which include a nut 352 which slides over a collet 353. The nut has diametrically opposed projecting bump or detent means 354 and a bead 355 on its interior surface and works as described for FIGS. 21 and 22. A barrel 356 is integral with the collet 353. The outer surface of barrel 356 has a head abutment 359 for engagement with the inside bump detent means 354. Collet 353 has radially disposed keys 357 which grasp a medicament cartridge 358. When the nut 352 is rotated and engages detent bump means 361 by projecting bump 354 to interlock the nut to the collet. A closed thread or ramp may be used in lieu of bump means 354 within the nut. The nut 352 is retained in the groove 362 between bead abutment 359 and gun barrel abutment 350 at all times.

FIG. 26 shows a longitudinal sectional view of the mounted cartridge and the nut fixed in place with the keys clamped to the cartridge and the nut in the clamping position. Also is shown a retracted cartridge-needle 363 on the plunger rod and captured by the male connector 323 of the cartridge grommet 322. Finger rings 314 are provided on the outside portion of the rearward portion of the barrel 306. A thumb ring 316 is provided on the outside end of the plunger rod. Thumb plate and finger flanges may be substituted for the rings.

FIGS. 27-33, INCLUSIVE

FIGS. 27-33 depict cartridge-needle combinations in which the needle may be retracted into the cartridge as shown in FIG. 26 or into the syringe containment means after use is complete for protected needle disposal purposes FIGS. 27-30 are cartridge-needle units, all of which are mounted from inside the containment means 371. These units do not have the conventional sealing disk 363 usually found in cartridges beneath the sheet metal foil cap means 368. The burden of a secure seal may be borne by the needle base providing a further cost savings to the cartridge manufacturer.

FIG. 27 shows a rear mounted cartridge-needle 364 having threaded section 365 for securing such needle within the hole or eye opening of the eye cap. The threaded section 365 has a tapered smooth of finned portion 366 which may be receive a close fitting cap 369 or 370 as shown in FIGS. 29 and 30 so that axial rotation can be applied to the needle by the cap to help unseat the needle to begin retraction into the cartridge shell 367. The base of the needle which resides within the cartridge has a female receiving cavity within a bell shaped base 372 which is fully surrounded by an O-ring grommet 373. The female receiving cavity could connect to the male fitment 323 of the plunger grommet 322 shown in FIGS. 22 and 24.

FIG. 28 shows a single beveled needle 374 with a threaded connector rearward extension 375 which is captured by the plunger tip threaded connector 319 of plunger rod 315 of FIGS. 22 and 24 upon removal of the cartridge grommet. A set of securing threads 376 are in engagement with the edges of the eye cap eye opening and secure the needle in usable position. A rubber base 377 extends rearward from the securing means 376 and totally fills the cavity at the inside top of the cartridge sheet metal foil cap means 368 to provide a secure sealing means between the needle and the glass containment means 371. Note that when use is complete, the needle shown in FIG. 28 may be captured by the plunger grommet threaded receiving cavity 394 as shown in FIG. 38. When fully tight, continuation of rotation of the plunger rod in the same direction as when capturing will cause the forward threads 376 to unseat for withdrawing the needle into the containment means.

FIG. 29 shows a special needle with a key lock mounting means 378 having a tight fitting cap 369 covering the needle and the key lock. The key lock is made of camming shoulders 379 which are inserted through the eye cap key hole 381 and then axially rotated to engage the surface of the eye cap as shown in FIG. 33. The rotation is 90 degrees an is limited by retaining bumps 382. Camming is not limited to the outside of the metal foil can and the needle base could be configured such that it occurs beneath or inside the sheet metal foil in which case the retaining bumps would be depressions in the foil surface. The needle is securely attached within the eye opening of the eye cap as shown in FIG. 33. The bell shaped needle base 383 in FIG. 29 is similar to the one in FIG. 27 and is provided with a shock absorbing and sealing O-ring grommet 384. In the same way that FIG. 33 shows an overhead top view of the key lock mounting system, FIG. 32 shows a similar view for the round threaded needle bases shown by FIGS. 27, 28, 30 and 31.

FIG. 30 shows a rear mounted needle 385 in a close fitting cover 369 and grommet as shown in FIGS. 22, 24 and 38. The close fitting cover is secured by a threaded projection hub 386 and long needle 387 into the eye opening 338 of sheet metal foil eye cap means 368 of containment 371 as shown in FIG. 32. The structure of the needle base that is within the sheet metal foil cap 368 includes a shock absorbing o-ring seal 389 which surrounds the bell shaped needle base 391. Inside bell 391 is female receiving chamber 392 for receiving male fitment 323 of plunger grommet 322 as introduced in FIGS. 22 and 234 and to be further described later in FIG. 38. Grommet 322 has a circumferentially disposed rebound boot 393 on the mating face of the grommet. The male fitment 322 is made of rubber or can be continuous with the threaded plunger mating piece 394 as shown in FIG. 38 and made of plastic or metal. The cartridge-needle of FIG. 30 is preassembled and contains fluid and is tightly capped for use in a dental syringe or other syringe apparatus.

In the operation of the cartridge-needle syringe device, a liquid medicament is injected in the usual way. At the end of use, the male fitment 323 is entered into the female receiving cavity 392 of FIG. 30 or 372 of FIG. 27 or 380 of FIG. 29 by fully depressing the plunger and compressing the rebound boot 393. This provides positive unification of structures so that, upon further rotation and unseating from the eye cap, the needle is retracted into the cartridge until the needle is fully encapsulated within the containment means. Proper disposal can be accomplished. Alternately, if an empty containment means 371 is used to aspirate fluids after mounting of the needle, the rebound boot may then be used as a kick-back means to allows disuion of the male fitment from the female receiving chamber all the while initiating self-aspiration upon release of the thumb plate or ring.

FIG. 31 is a longitudinal sectional view of a front mounted double-beveled needle that may be retracted or captured within the containment means after use and will be described with a special coaxial cap-needle mounting system to follow.

FIGS. 34–37, INCLUSIVE

FIGS. 34–37 inclusive, show a coaxial, non-coring cap-needle device and how it may be used for non-coring needle penetration of the rubber membrane disk of a cartridge or syringe sheet metal foil cap and subsequent fastening of the needle structure within the eye opening of the eye cap. Such manner of mounting a needle has useful advantages over the prior art two step devices providing needle and medicament segregation prior to use.

FIG. 34 illustrates non-coring needle mounting and protection capability for handling of double beveled needles that are mounted to pre-packaged medicament syringes and cartridges. A modified cap-needle assembly 401 is a needle holder and mounting device combined. A double beveled needle 402 is snap detent fitted within a center cap 403. Needle 402 is provided with a truncated conical swaging and fastening means 404 outside the needle base 405 and through which the shorter needle 406 projects. Needle base 405 is a truncated cone with a smooth portion 407 and a finned portion 408 through which long needle 409 extends. Surrounding the long needle is a center cap 403. Cap 403 is shaped to protect the needle and drive the needle during fastening to the eye cap. A bottom apron 415 surrounds the top or smooth portion of the needle base. A small diameter cap with a prong formed about the finned portion 408 could allow the capped needle to be mounted from inside the dental syringe holder so that the cap might subsequently be removed from the outside at the time of use. In the area of the fins 408 of the longer needle 409, the inside of center cap 403 is provided with corresponding mating fins which together form a camming means. On the outside surface of center cap 403 is a detent groove means 412 in the center cap cooperating with bead 414 on the cap ferrule 413 for securing the center cap 403 with needle 402 segregated from the contents of the containment means prior to use. An extension 426 extending from the cap ferrule in this area will provide a reliable taper seal with the center cap prior to use. The smooth base 407 terminates into apron 415 of center cap 403 extending outwardly therefrom. Guide runners 416 on the exterior of center cap 403 adjacent the apron 415 and mesh with mating guide runners 417 in the inside of cap ferrule 413 to form a spline system which enables anti-coring penetration of the disk membrane 418 of the eye cap and containment means. Non-coring assurance may also be provided with a ferrule having a non-circular opening provided for center cap passage. This embodiment is shown in FIG. 34A.

The cap ferrule 413 is attached to the eye cap 419 which is the tip of a cartridge or syringe prefilled with medication. The cap cylinder 413 is dimensioned so as to receive the eye cap 419 of containment means 421. The structure of the eye cap 419 is such that a groove 42 may be present and is defined by the clamping area of the eye cap to the containment means 421. The cap ferrule 413 has internal detent means 423 which corresponds to this groove to secure the cap-needle assembly 401 to the containment means 421. Otherwise, the detent may be found higher up in the ferrule to act as a stop for the standard eye cap cover as shown in FIG. 35. Another variation of the standard eye cap covering is to form a metal tube extension in place of the eye opening. Such extension would support two step mounting of a corresponding needle base.

FIGS. 35 and 36 show alternatives to the swaging-pawl fastener 404. A threaded swage fastener 425 is shown in FIG. 35. A key lock fastener 424 is shown in FIG. 36. Other fastener means may contain snap, pawl, thread, bulge, swage or other securing means for attachment. FIG. 31 shows the structure of a cartridge-needle that might be mounted using the coaxial cap-needle system as shown in FIGS. 34 or 34A. A swaging base 436 has a detent means 428 to engage the opening in eye cap 419. This includes a threaded extension 427 and is available to be captured by a plunger means as shown in FIG. 38. The grommet includes a mating screw means to attach and retract the needle through the eye cap 419 and into the cartridge or syringe body. A nut may be fastened to threads added to needle base 431 if added stability is needed. A pawl mechanism may help to anchor the needle base into the glass wall of the syringe tip. On the long needle 429 side is a finned or smooth section 431 where a needle or center cap can provide a snug fit to detent groove 432. A cap ferrule could then be passed off and discarded after the needle is mounted and the center cap left to protect the long needle until just prior to use. Or the now mounted cap-needle glass containment combination may the be readily used in syringe assemblies or dental syringes to follow.

FIG. 34A shows an alterative coaxial cap-needle where a non-circular opening in the cap ferrule 413' allows passage of the center cap 403'. The hex shaped opening in the cap ferrule 413' allows passage of the center 403'. The hex shaped opening, used for convenient, allows the center cap corresponding facet ring 417' above the center cap apron 415' to perform as the spline system to allow non-coring penetration of eye cap disk member by the short needle in that axial rotation of the needle is prevented as the disk membrane is pierced during the center cap facet ring passage through the ferrule opening. Once the disk membrane is penetrated, the center cap needle may be freely rotated.

In the operation of the coaxial cap-needle system, the assembled cap is removed from the short needle cover cap if the system is separate from the medication-laden packaging. The coaxial cap is mounted on the sterile eye cap 419 of the containment means 421. A paper or heat detent seal between cap ferrule 413 as part of extension 426 and the center cap 403 is broken when mounting is desired and the center cap is then depressed so that the guide runners or ring facets 416 and 416' and corresponding runner 417 move by one another. For a screw fitting needle fastener, full center cap rotation is allowed once the short needle 406 has fully penetrated the disk membrane 418. At that time, the center cap 403 may be axially rotated to engage the threaded connector 425 with the eye cap opening and completely tightened until the needle base 405 and apron 416 make secure contact with said eye cap as shown in FIGS. 35 and 36. The mounted needle is thereby stabilized and securely connected. However, one may not retract and protect a needle within the containment means if base 405 is larger in diameter than the containment means tip diameter or the needle will not separate from the base. Therefore, a cap handle device as shown in FIG. 47 or barrel safety shell of FIG. 48 might be provided with the cartridge-needle syringe holder as an alternate means for protection. With the cap ferrule removed as described previously, the remaining structure will fit easily into an injector assembly or dental syringe holder to form a combination cartridge-needle syringe apparatus. The swaging or pawl connector needle 435 a described and shown in FIG. 31 can be removed or mounted from either the inside or outside of containment means 371. The swaging base 436 when mounted form outside or the finned or smooth section 431 if mounted from inside may be used to swage the metal of the eye cap opening from either direction. A swaging type base would not need to be axially rotated as are the threaded bases. In these style bases, guide runners 416 and 417 or facet ring 417' may be provided in registry with corresponding ferrule receiving parts throughout the entire slide mounting process.

FIGS. 38-52A INCLUSIVE OPERATION

FIGS. 34-52 show various embodiments of the invention as practiced when a dental syringe cartridge-needle holder or glass syringe and holder handle recap means are used.

FIG. 38 shows the details of the grommet 322 which fits within dental cartridges for containment and fluid delivery. A male fitment 323 is on the forward face of the grommet for for engaging the female receiving chamber of a needle. Within male fitment 323 is shown a threaded cavity 394 which may be used to mate with threaded needle extension 375 as shown in FIG. 28. On the opposite end of the grommet, a threaded male plunger mating means 321 is available for uniting with a plunger tip mating means of a plunger rod as used in the syringe assemblies previously described. Alternatively, the face of the grommet can be solid without any projection or cavity as conventionally utilized. In such cases, a harpoon mounted on the plunger without the grommet in place as shown in FIG. 42, may be used to fasten to the grommet. Grommet 322 has constrictions 441 between the ends thereof for shock absorbing and sliding purposes. A rebound boot added will give shock absorbing action to extreme. Such boot 393 located circumferentially disposed around the edge of the forward face of the grommet, extends toward the needle. An earlier showing of the boot is shown in FIG. 29.

FIG. 39 is an overhead longitudinal view of a self-aspirating dental syringe 501 which may be loaded with a cartridge 367 or cartridge-needle combination as previously described and an example of which is shown in FIGS. 49-51. The dental syringe 501 comprises a cylindrical barrel 502 defining a cavity 503 which receives a cartridge 367 or any of the cartridge-needle combinations as described. Barrel 502 is commonly formed with one or more axially extending aperatures 504 in its wall. These aperatures assist insertion, removal and viewing of cartridge or cartridge-needle combinations. The forward end of the barrel 502 is truncated, conical and open as shown in FIGS. 40 and 43. The threaded syringe tip 531 of syringe barrel 502 allows for conventional double beveled needle attachment from inside by using runners or longitudinal grooves 532 that correspond with runners on the outside of a needle hub or base in which case a bayonette means may be provided. External tip threads 538 may be used for attaching corresponding needle hubs. A novel bump or ramp detent means between threads may also be provided as previously described. The needle might be mounted in either case using female receiving fitment 525 of the plunger piston 526. The structure allows for latitude in selecting a desired needle base structure or cartridge-needle combination as previously described for retracting the needle or combination into the barrel of the syringe after use.

A fitting adapter 505 formed with a central axially directed screw-threaded spigot 506 as shown in FIG. 41 may be threadedly attached to the truncated forward conical end of the barrel by the rear threads 507 of the fitting adapter. With the fitting adapter 505 secured to the threaded barrel tip 531, the standard double beveled needle hub may be attached to the screw threaded spigot 506.

On the attachment face of the fitting adapter 505 is an opening 508 formed with a central stud 509 which projects rearwardly into the cavity 503. The short end of the needle extends rearwardly from the hub through an axial ore 511 in the fitting adapter 505 into the cavity 503 beyond the stud 509. A front compression spring may be left out whereby the action it provides is then fully assumed by the rubber disk membrane seal means in the eye cap of the cartridge used. A double beveled needle may be provided with a hub configured like the fitting 505. The front compression spring 512 may also project from the attachment face of the fitting 505 to provide a cushion surrounding the central stud 509. Cartridge-needle combinations as previously described, may be loaded into the syringe while the syringe barrel tip means remains open for receiving rear mounted needles.

The rear end of the syringe barrel 502 is received in a pivot fitting 513 which carries a pair of laterally extending finger grips or depressions 514. A barrel sleeve 515 within the finger depressions house a slidable bushing 516 surrounded by a rear compression spring 517 as shown in the partial sectional view of FIG. 39. The bushing 516 extends through an axial hole in threaded washer stabilizer 518, has a rear flanged head 519 of bushing 516 which is guided for reciprocating movement by the cylindrical inner surface of the barrel sleeve 515. Either the front flange head 522 or the rear flange head 519 of bushing 516 has a front recess 523 for receiving the rear part of a cartridge containment means. The busing bore is further constricted into a secondary front recess 524 for receiving the fitment 525 female cavity of plunger piston rod 526. Plunger piston 526 passes through the rear end of the syringe barrel as described and may terminate in a thumb plate or ring 527.

FIGS. 44 and 45 are of various mixing containment shells. Containment shell 542 in FIG. 44 is provided with constriction 546 to provide a stop for the cartridge so that cartridges or syringes bay be back loaded, removed and exchanged. Spline keys 547 may be used as could keys 543 as part of a center cap of a coaxial cap-needle system. FIG. 45 shows containment shell 541 which is provided with spline keys 543 which receive fins 544 of a double-beveled needle as shown in FIG. 48 to allow non-coring entry between a cartridge or syringe-needle combination and the cartridge 367 contained therein. Fluids may be passes back and forth between containments. In this way, all cartridges or containment means and needles may be dept segregated and even pristine and subsequent mixing of medicaments may be reliably performed using non-coring sterile technique at the same time that use and mixing is desired.

FIG. 46 is a sectional view of the tip of a glass containment syringe 451 which bayonette needle mounting ferrule 452 fastened into the inside of the glass containment 453. The mounting ferrule 452 will accept a standard needle base with ovate flange and may be mounted by a corresponding glass male fitment and mounting pedestal of a glass syringe plunger piston. The ferrule 452 is formed to conform to the shape of a standard needle and consists of a flange housing 443, primary constriction and outside abutment 444, tapered base portion 445 which may contain along its length a back-up sealbead 446. The tapered base portion 446 is followed by a secondary constriction and outside abutment 447 which turns into and ends with a luer-slip extension tube 448. The ferrule has a bayonette mounting cutouts 454 placed in opposition within the flange housing section 443. The cut-outs have a straight inroad 455 which makes an abrupt 90 degree turn into a lock pathway 456. Pathways are pointed in opposite directions from each other in order to receive the needle ovate flange together. Each pathway has a constriction point 457 which gives a tactile signal to the operator as the ovate flange of the needle moves by to its locked and sealed mounted position area 458. The operation of the glass luer syringe corresponds to that previously described for the syringe of FIGS. 1-6.

FIG. 47 shows a longitudinal view of a prefolded cap handle device 651. One or more angle fold marks are indicated by dotted liens 652 and 653. Attachment rings 654 and 655 are located at either end of the device. Large attachment ring 654 is appropriately sized to pass over a syringe barrel or similar device mounted with a needle. Small ring 655 may adapt to a standard needle cap. Each ring may be incomplete to cause it to make the shape of the letter C. This would make snap fitting to the syringe barrel or cap more convenient and possible from the side of the cap or barrel. Bits 656 and 657 may be removed or one or both sides left intact with the ring to allow for a gating mechanism.

The cap handle allows an alternative for recapping a needle in a syringe or a needle containing apparatus. Syringes not provided with an easy means of protecting the needle after use is complete could be protected with the handle. The handle could be offered as a premounted accessory or provided separately for mounting prior to needle attachment in a syringe or needle holder. The cap handle would allow the user to recap or remove the cap from a mounted needle such that the user's hands remain behind the needle at all times. It also allows the user a convenient and useful means to keep track of a needle cover during the use of the needle containing apparatus.

FIG. 48 illustrates a cartridge-needle combination within a finned containment shell 534 into which a cartridge, needle or cartridge-needle combination might be retracted following use. Fins 535 contain a detent means 536 for receiving a needle flange 537 so that a needle may be securely and irreversibly retracted into the containment shell after use. The containment shell allows for an alternate means of protecting a needle should a needle not be capable of alternate protection.

In the method of the operation of a retractable, self-aspirating dental syringe as shown in FIG. 39, a needle is first mounted inside the syringe barrel tip. The short needle would contain a central stud 509. A compression spring may also be provided within the needle hub or barrel tip depending on needle form sued. Once the needle is secured in the syringe tip with center cap still in place for protection, a cartridge is then loaded from behind in a broken down syringe as shown in FIG. 51. Alternately, loading may be effected by passing a cartridge through aperature 504 in the braced syringe of FIG. 39. In the braced position, the plunger piston may be attached to the cartridge grommet by using female receiving fitment 525 to receive male connector 321 of the sealing grommet if provided or, by first attaching harpoon fitment 528 as shown in FIG. 42 to female receiving fitment 525. The syringe as provided need not specify that the plunger piston be securely attached to the sealing grommet by what ever means in order to still be self-aspirating. However, in order to have greater control over the sealing grommet and for retracting a needle into a cartridge or syringe containment means, the piston rod 526 must be securely attached to the sealing grommet.

Once the syringe cartridge is loaded and ready to use, the rear flanged head 519 of slidable bushing 516 may be thumb depressed to relieve pressure on rear compression spring 512 if provided and central stud 509 causing the rubber membrane disk inside the cartridge eye cap to be compressed or displaced in the rearward direction. This causes fluid within the cartridge to be expressed or displaced from the needle and any entrained air inside the cartridge may be vented at this time. An aspirating or negative pressure is then contained within the cartridge and the needle may now be hypodermically placed in gum or other body tissue. Upon subcutaneous entry, the needle is sealed and it is no longer necessary to keep the rear flange head 519 of the slidable bushing 516 depressed. The vacuum seal is strong enough to overcome the resilient compression of the springs and sealing disk or membrane of the cartridge eye cap and front compression spring if used until a vessel is entered by the needle at which time the user may see a blood flashback through the syringe aperature 504 or the rear flange head of the bushing 516 fall back to its resting position. A locking or retaining means for the slide bushing 516 may be provided but is left out here for simplicity. The syringe is then used in conventional fashion by depressing the plunger piston for injection of medicament as desired.

Upon completion or full dispensation of cartridge contents, a cartridge might be removed and replaced with a fresh cartridge. The needle remains firmly anchored in the syringe tip in this case. FIG. 50 depicts removal of the combination cartridge and needle. If the containment shell shown in FIG. 48 is utilized, a cartridge and needle might be retracted into it for safe disposal. A cap handle as shown in FIG. 46 may be provided as a means of recapping a used needle in a safe manner. FIG. 52 shows such a needle with a cap and base configuration which might be used as described. The needle cap as shown, contains a threaded or otherwise truncated spade or wedged shaped tip which may be adapted to a corresponding female receiving pocket of a cartridge or syringe grommet so that the cap may thereby be used also as the plunger piston means. After use is complete, the cap may be joined to a cap handle device as previously described for safe recapping after use.

FIG. 52A shows another syringe accessory which comprises an alternate means for attaching finger flanges to the glass barrel of a syringe or cartridge when a syringe assembly is not available. Such a syringe barrel flange retaining boot 551 consists of a shell casing wall 552 with finger flange extensions 553. The interior of the shell casing portion contains a detent bead 554 which snaps into the corresponding groove 395 at the end opposite the tip of the syringe barrel as shown in FIG. 29. An abutment lip 555 acts as a back stop to retain the back of the containment means barrel and plunger piston grommet. Extension pegs 556 attach to flex ring 557 which is tethered to attachment base 558 which turns into and becomes a part of the abutment lip 555.

In the operation of the flange retaining boot 551 accessory, a glass containment means having a groove 395 is medication-laden and ready for dispensing. The flange retaining boot may be provided attached or attached by being manually snapped on to the glass barrel at this time. A double-beveled needle is attached to the syringe eye-cap by coaxial mounting cap assembly or from inside the barrel by the manufacturer. Note that a hollow plastic needle and cannula may be less likely to core as only its point is used for penetration. Flex ring 557 may be pulled to break extension pegs 556 for hanging purposes or a plunger piston attached to the syringe grommet whereby the flex ring acts as reinforcement for the plunger as it slides axially and rotatably through or passed during dispensing of contents. The flange retaining boot may be thrown away with the dispensed syringe barrel or pulled from the syringe barrel retaining groove 395 for use with the following syringe vial packaging.

FIGS 53–60, INCLUSIVE OPERATION

FIGS. 53–60 show various embodiments of the invention used for blood drawing purposes. A needle holder-dropper is a modified syringe barrel used to firmly hold a double-beveled blood drawing needle which is commercially available and well known to the industry. The long needle is hypodermically inserted into a vein. The short needle is covered with a protective boot and used to pierce the rubber grommet tip of a blood drawing evacuated tube. Multiple tubes may be collected in a single patient. Holders are often reused after needles are removed by a wrenching means when using exiting holders.

FIG. 53 illustrates the holder-dropper device for handling of double-beveled blood drawing needles. A modified syringe barrel 601 is a needle holder and dropping device combined. In use, a double beveled needle 602 is placed in operative position by opening the threaded needle mounting end 603 of the barrel 601. The standard needle 60 has a solid, threaded projection 604 for clamping the threaded portion of the finned needle base 605. These base fixtures are reversed should mounted from inside the hallway of the device be desired. The threaded projection 604 has an annular configuration that is integral with the tube enclosure 606 and hallway 616 of annular configuration having a circular or oval outer shape. This enclosure is integral with the tubular barrel wall 607. The hallway is the empty space inside the closure into which tubes are inserted. A slot 608 is provided along the minimum outside diameter of tube enclosure 606 through the needle mounting end 602 and continues through the thinnest section of the tubular barrel 607 to a pivot point 609 along the barrel wall. This pivot 609 might be a slit enlargement. Surrounding the pivot is a circular ridge of plastic or target bead 622 used to both reinforce the area around the pivot and used as a guide for finger and thumb during the mounting and dismounting of a needle. Thumb and fingers may otherwise be positioned below the pivot. The slot 608 is dimensioned so as to be able to open threaded projection 603 enough to accommodate the dropping and mounting of the needle base. The depressions 611, if included, indicate the position of the thumb on one side and the index and middle fingers on the opposite side of the barrel. If side walls are not uniformly thin, this position in in the thinnest part of the side wall 607 and proximal to the pivot 609 on the side away from the slot. Otherwise, the target beads themselves may be pressed together to cause opening for needle mounting and relaxed to cause clamping to the needle base. A conventional finger plate or flange 612 protrudes from the barrel at the end distal from the needle mounting end 603 and can be used to stand the device on end.

In the operation of the needle holder-dropper 601, the user presses on depressions 611 or sidewall below the slits or the target beads 622 and thereby opens the threaded projection 603 to receive the correspondingly threaded base 604 of double-beveled needle 602. The short needle 613 is protected by a rubber boot 615. The standard needle is depicted as mounted from outside the holder-dropper device in FIGS. 53 and 55. A modified needle 68 with standard fixtures reversed for mounting from inside the hallway is shown in FIG. 59. In applications where this device is to be used to draw blood, an evacuated tube is inserted into the barrel hallway 616 and is urged over the short needle 613 compressing and piercing the rubber boot 615 and the rubber stopper of the evacuated tube. After filling is complete, the now filled tube is removed from the barrel. Other evacuated tubes may be filled and removed. Evacuated tube 614 is formed from a cartridge ampule and may be used in a normal sized holder-dropper if a tubular busing were first inserted to better accommodate the smaller diameter of the cartridge. The needle is removed from the vein after blood drawing is complete and depressions 611 if included, are again depressed to drop the needle from the device into a conical chamber 617 as shown in FIG. 57. The needle may be dropped through hallway 616 if the needle is mounted from inside the holder-dropper in which case its base fixtures are reversed as shown in FIG. 59. The device is then available to be used with another needle. Of course, one is not restricted in how either standard or reversed needle base needle is dropped from a holder-dropper.

In a modification wherein the needle is mounted from the inside of the barrel, as shown in FIG. 59, a needle 618 with base fixtures reversed is required. This is accomplished by reversing the screw threaded base 619 and the finned sleeve 621. The needle is then mounted in the encapsulation chamber 625 within oval opening 626 at the mounting end thereof. The opposite end of the chamber 625 is sealed. On the interior of encapsulation tube 625 are projecting teeth 627 of such dimension and position as to capture a used needle to be protected for disposal.

The operation of the inside mount encapsulation chamber 625 is not limited to use with needle that are mounted from inside the needle holder. With the needle cap removed, the long needle end is pushed through the needle mounting end 603 of the needle holder 610 and thereby seated from inside by threaded projection 619. The encapsulation chamber 625 is then removed allowing for the intended use, the drawing of blood. When use is completed, the needle may be recaptured by placing the chamber 625 over and about the finned sleeve 621 of needle 618. Threaded needle mounting end 603 is opened by squeezing the holder side walls, and the encapsulation chamber 625 with captured needle 618 are together withdrawn from hallway 616 within barrel 601. When the structure around oval opening 626 is depressed into a round configuration, the needle will cease to be captured and will fall or be swallowed into chamber 625 and there protected by the projecting teeth 627 as shown in FIG. 59. The encapsulated needle is now ready for disposal.

The blood drawing tube 614 of FIG. 58 is a modified cartridge ampule where the evacuated containment means and sealing grommet are fixed to a retaining wheel 628 containing a threaded center hole 629. The wheel overlaps the cartridge side walls and is threadedly attached to the male threaded fitment of the grommet. The wheel and sealing grommet may be removed jointly in order to gain access to the interior of the cartridge ampule for blood analysis or the like. Otherwise, the disk membrane or plunger grommet may be pierced with a hypodermic needle for fluid aspiration thereof. Removing the wheel 628 facilitates aspiration of material from the eye cap and membrane disk side of the cartridge ampule.

From the foregoing, it will be seen that this invention is one well adapted to attain all the ends and objects hereinabove set forth together with other advantages which are obvious and which are inherent to the apparatus.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawing is to be interpreted as illustrative and not in a limiting sense.

I claim:

1. An article of manufacture comprising a barrel having at the distal end a needle attached thereto, said needle having a male threaded rearward extension that extends into said barrel, said barrel having at the proximal end an opening into which there is fitted a plunger, said plunger having a its distal end a grommet seal and a female threaded accepting cavity for accepting the rearward extension of the needle.

2. An article of claim 1 wherein the rearward extension has a point which punctures the grommet seal when the rearward extension of the needle is accepted in the threaded accepting cavity of the plunger.

3. An article of claim 1 wherein the female accepting cavity is covered by a portion of the grommet.

4. An article of claim 1 wherein the distal end of the needle attached to the barrel is separable from the rearward portion of said needle that extends into the barrel.

5. An article of claim 1 wherein the sealing grommet is punctured when the rearward portion of the needle is accepted into the female accepting cavity of the plunger.

6. An article of claim 1 wherein the plunger is readily breakable after partial retraction from the barrel.

7. An article of claim 1 wherein the needle is attached to the barrel using a co-axial mounting device.

8. A method of rendering a syringe and needle non-reusable by securing a male threaded rearward extension of the needle assembly into a complementary threaded female accepting cavity on the distal end of the plunger, said plunger having at its distal end a seal which is punctured when said male threaded rearward extension of said needle assembly is secured in said threaded female accepting cavity on said plunger, and retracting said needle into the barrel of said syringe.

9. A method of claim 8 wherein, after the needle has been retracted into the barrel of the syringe, the plunger is broken.

10. A method of claim 8 wherein the seal is a grommet seal.

11. A method of claim 8 wherein the barrel is a cartridge used in a syringe holder, the plunger consists of a shaft and a seal, wherein at least part of said shaft is disconnected from said seal after the needle has been retracted into the barrel.

12. A method of claim 11 wherein the seal is a grommet seal.

* * * * *